(12) United States Patent
Boettcher et al.

(10) Patent No.: US 9,173,581 B2
(45) Date of Patent: Nov. 3, 2015

(54) APPARATUS AND METHOD FOR THE AUTOMATED MEASUREMENT OF SURAL NERVE CONDUCTION VELOCITY AND AMPLITUDE

(75) Inventors: Bonniejean Boettcher, Maynard, MA (US); Marc Cryan, Maynard, MA (US); Shai N. Gozani, Brookline, MA (US); Glenn Herb, Weston, MA (US); Xuan Kong, Acton, MA (US); Michael Williams, Melrose, MA (US); Charles Fendrock, Sudbury, MA (US)

(73) Assignee: NeuroMetrix, Inc., Waltham, MA (US)

( * ) Notice: Subject to any disclaimer, the term of this patent is extended or adjusted under 35 U.S.C. 154(b) by 533 days.

(21) Appl. No.: 13/235,258

(22) Filed: Sep. 16, 2011

(65) Prior Publication Data

US 2012/0101358 A1    Apr. 26, 2012

Related U.S. Application Data

(60) Provisional application No. 61/403,453, filed on Sep. 16, 2010, provisional application No. 61/459,127, filed on Dec. 6, 2010, provisional application No. 61/467,857, filed on Mar. 25, 2011, provisional application No. 61/516,944, filed on Apr. 11, 2011, provisional application No. 61/571,203, filed on Jun. 22, 2011.

(51) Int. Cl.
  *A61B 5/05*   (2006.01)
  *A61B 5/04*   (2006.01)
  *A61B 5/00*   (2006.01)
  *A61B 5/01*   (2006.01)

(52) U.S. Cl.
  CPC .............. *A61B 5/04001* (2013.01); *A61B 5/05* (2013.01); *A61B 5/4041* (2013.01); *A61B 5/01* (2013.01);

(Continued)

(58) Field of Classification Search
  CPC ........... A61B 5/04001; A61B 5/04004; A61B 5/0488; A61B 5/4029; A61B 5/4041; A61B 5/47047; A61B 5/4052; A61B 5/4893; A61B 5/6828; A61B 5/6829; A61B 5/6844; A61B 5/6835; A61B 2560/028; A61B 2560/0285; A61B 2560/0406; A61B 2560/0431; A61B 2560/0468; A61B 2560/0475; A61B 2562/0209; A61B 2562/08
  USPC ................. 600/372, 382, 384, 393, 554, 557; 607/144, 145, 150, 151; D24/168, 170, D24/187
  See application file for complete search history.

(56) References Cited

U.S. PATENT DOCUMENTS 2,327,874  A  *  8/1943  De Jong ........................ 607/150
D243,417  S  *  2/1977  Allen et al. ................... D24/187

(Continued)

FOREIGN PATENT DOCUMENTS

JP       S60-194933       10/1985

OTHER PUBLICATIONS

Albers et al., Subclinical Neuropathy Among Diabetes Control and Complications Trial Participants Without Diagnosable Neuropathy at Trial Completion, Diabetes Care, Oct. 2007, pp. 2613-2618.

(Continued)

*Primary Examiner* — Linda Dvorak
*Assistant Examiner* — Erin M Cardinal
(74) *Attorney, Agent, or Firm* — Pandiscio & Pandiscio

(57) ABSTRACT

Apparatus for measuring sural nerve conduction velocity and amplitude, the apparatus including a housing; stimulation means for electrically stimulating a human sural nerve; a biosensor comprising a plurality of electrodes for detecting a sural nerve response evoked by the stimulation means; acquisition means electrically connected to the biosensor for electrically acquiring the sural nerve response detected by the biosensor; processing means electrically connected to the acquisition means for digitizing, processing and storing the acquired sural nerve response; calculation means electrically connected to the processing means for calculating the conduction velocity and amplitude of the processed sural nerve response; and display means for displaying the sural nerve conduction velocity and amplitude; wherein the stimulation means and the biosensor are designed to be placed on a patient's anatomy, in the vicinity of a sural nerve.

71 Claims, 15 Drawing Sheets

(52) U.S. Cl.
CPC . *A61B 2560/0425* (2013.01); *A61B 2560/0468* (2013.01); *A61B 2562/0209* (2013.01); *A61B 2562/046* (2013.01)

(56) References Cited

U.S. PATENT DOCUMENTS

| | | | |
|---|---|---|---|
| 4,033,356 A * | 7/1977 | Hara | 607/152 |
| 4,121,573 A | 10/1978 | Crovella et al. | |
| D255,938 S * | 7/1980 | Hawke et al. | D24/187 |
| 4,419,998 A | 12/1983 | Heath | |
| D299,746 S * | 2/1989 | Guldalian, Jr. | D24/186 |
| 5,215,100 A | 6/1993 | Spitz et al. | |
| 5,327,902 A | 7/1994 | Lemmen | |
| 5,755,750 A | 5/1998 | Petruska et al. | |
| 5,851,191 A | 12/1998 | Gozani et al. | |
| 5,991,355 A | 11/1999 | Dahlke | |
| 6,298,255 B1 | 10/2001 | Cordero et al. | |
| 6,312,392 B1 * | 11/2001 | Herzon | 600/554 |
| 7,459,984 B2 | 12/2008 | Wang et al. | |
| 7,760,428 B2 | 7/2010 | Sieckmann | |
| 7,844,325 B2 * | 11/2010 | Takehara | 600/547 |
| 7,917,201 B2 | 3/2011 | Gozani et al. | |
| D638,131 S * | 5/2011 | Buckels et al. | D24/187 |
| 2002/0173828 A1 | 11/2002 | Gozani et al. | |
| 2003/0093006 A1 | 5/2003 | Wells et al. | |
| 2006/0020291 A1 | 1/2006 | Gozani et al. | |
| 2007/0129771 A1 | 6/2007 | Kurtz et al. | |
| 2007/0149892 A1 | 6/2007 | Guldalian | |
| 2007/0185409 A1 | 8/2007 | Wu et al. | |
| 2007/0219441 A1 | 9/2007 | Carlin et al. | |
| 2008/0288026 A1 * | 11/2008 | Cross et al. | 607/60 |
| 2012/0226186 A1 * | 9/2012 | Baars et al. | 600/554 |

OTHER PUBLICATIONS

Behse et al., Sensory Action Potentials and Biopsy of the Sural Nerve in Neuropathy, Brain, 1978, pp. 473-493.
Behse et al., Nerve Biopsy and Conduction Studies in Diabetic Neuropathy, Journal of Neurology, Neurosurgery, and Psychiatry, 1977, pp. 1072-1082.
Benatar et al., Reference Data for Commonly Used Sensory and Motor Nerve Conduction Studies, Muscle & Nerve, Nov. 2009, pp. 772-794.
Boulton et al., Diabetic Neuropathies, Diabetes Care, Apr. 2005, pp. 956-962.
Burke et al., Sensory Conduction of the Sural Nerve in Polyneuropathy, Journal of Neurology, Neurosurgery, and Psychiatry, 1974, pp. 647-652.
Charles et al., Low Peripheral Nerve Conduction Velocities and Amplitudes Are Strongly Related to Diabetic Microvascular Complications in Type 1 Diabetes, Diabetes Care, Dec. 2010, pp. 2648-2653.
Dros et al., Accuracy of Monofilament Testing to Diagnose Peripheral Neuropathy: A Systematic Review, Annals of Family Medicine, Nov./Dec., 2009, pp. 555-558.
Dyck et al., Clinical and Neuropathological Criteria for the Diagnosis and Staging of Diabetic Polyneuropathy, Brain, 1985, pp. 861-880.
Dyck et al., Fiber Loss Is Primary and Multifocal in Sural Nerves in Diabetic Polyneuropathy, Annals of Neurology, May 1986, pp. 425-439.
Dyck et al., Signs and Symptoms Versus Nerve Conduction Studies to Diagnose Diabetic Sensorimotor Polyneuropathy: Cl Vs. NPhys Trial, Muscle & Nerve, Aug. 2010, pp. 157-164.
England et al., Distal Symmetrical Polyneuropathy: A Definition for Clinical Research, Neurology, Jan. 2005, pp. 199-207.
Esper et al., Sural and Radial Sensory Responses in Healthy Adults: Diagnostic Implications for Polyneuropathy, Muscle & Nerve, May 2005, pp. 628-632.
Gibbons et al., Diabetic Neuropathy, A Cross-Sectional Study of the Relationship Among Tests of Neurophysiology, Diabetes Care, Dec. 2010, pp. 2629-2634.
Gordois et al., The Health Care Costs of Diabetic Peripheral Neuropathy in the U.S., Diabetes Care, Jun. 2003, pp. 1790-1795.
Harrison et al, The Neuropathic Factor in the Aetiology of Diabetic Foot Ulcers, Journal of the Neurological Science, 1976, pgs. 217-223.
Herman et al, Underdiagnosis of Peripheral Neuropathy in Type 2 Diabetes, Diabetes Care, Jun. 2005, pp. 1480-1481.
Kihara et al., Comparison of Electrophysiologic and Autonomic Tests in Sensory Diabetic Neuropathy, Clinical Autonomic Research, Aug. 1998, pp. 213-220.
Kirkman et al., Impact of a Program to Improve Adherence to Diabetes Guidelines by Primary Care Physicians, Diabetes Care, Nov. 2002, pp. 1946-1951.
Kiziltan et al., Peripheral Neuropathy in Patients With Diabetic Foot Ulcers: Clinical and Nerve Conduction Study, Journal of the Neurological Sciences, 2007, pp.75-79.
Kong et al., Utilization of Nerve Conduction Studies for the Diagnosis of Polyneuropathy in Patients With Diabetes: A Retrospective Analysis of a Large Patient Series, Journal of Diabetes Science and Technology, Mar. 2008, pp. 288-274.
National Diabetes Fact Sheet, Department of Health and Human Services, Centers for Disease Control and Prevention, 2007.
Pambianco et al., Risk Factor Associations With Clinical Distal SyrrirnetriCal Polyneuropathy and Various Neuropathy Screening Instruments and Protocols in Type 1 Diabetes, Diabetes Research and Clinical Practice, 2011, pp. e15-e20.
Pambianco et al., The Assessment of Clinical Distal Symmetric Polyneuropathy in Type 1 Diabetes: A Comparison of Methodologies From the Pittsburgh Epidemiology of Diabetes Complications Cohort, Diabetes Research and Clinical Practice, 2011, pp. 280-287.
Perkins et al., Glycemic Control Is Related to the Morphological Severity of Diabetic Sensorimotor Polyneuropathy, Diabetes Care, Apr. 2001, pp. 748-752.
Perkins et al., Validation of a Novel Point-of-Care Nerve Conduction Device for the Detection of Diabetic Sensorimotor Polyneuropathy, Diabetes Care, Sep. 2006, pp. 2023-2027.
Perkins et al., Multi-Site Testing With a Point-Of-Care Nerve Conduction Device Can Be Used in an Algorithm to Diagnose Diabetic Sensorimotor Polyneuropathy, Diabetes Care, Mar. 2008, pp. 522-524.
Russell et al., Sural Nerve. Myelinated Fiber Density Differences Associated With Meaningful Changes in Clinical and Electrophysiologic Measurement, Journal of the Neurological Sciences, 1996. pp. 114-117.
Standards of Medical Care in Diabetes—2006, Diabetes Care, Jan. 2006, pp. S4-S42.
Stetson et al., Effects of Age, Sex, and Anthropometric Factors on Nerve Conduction Measures, Muscle & Nerve, Oct. 1992, pp. 1095-1104.
Trojaborg et al., Sural Nerve Conduction Parameters in Normal Subjects Related to Age, Gender, Temperature, and Height: A Reappraisal, Muscle & Nerve, Jun. 1992, pp. 666-671.
Veves et al., The Relationship Between Sural Nerve Morphometric Findings and Measures of Peripheral Nerve Function in Mild Diabetic Neuropathy, Diabetic Medicine,1991, pp. 917-921.
Vinik et al., Sural Sensory Action Potential identifies Diabetic Peripheral Neuropathy Responders to Therapy, Muscle & Nerve, Nov. 2005, pp. 619-625.
Vrancken et al., The Realistic Yield of Lower Leg SNAP Amplitudes and SRAR in the Routine Evaluation of Chronic Axonal Polyneuropathies, J Neurol, 2008, pp. 1127-1135.
Wald et al., On a Test Whether Two Samples Are From the Same Population, The Annals of Mathematical Statistics, 1940, pp. 147-162.
Buschbacher, Sural and Saphenous 14-cm Antidromic Sensory Nerve Conduction Studies, Americal Journal of Physical Medicine & Rehabilitation, 2003, 82:421-426.
Boettcher, Bonniejean et al., A Rapid, Low-cost, Point-of-care Test for Diabetic Peripheral Neuropathy, Jun. 24, 2011.
Kong, Xuan et al., Repeatability of nerve conduction measurements derived entirely by computer methods, BioMedical Engineering OnLine, 2009, 8:33.

* cited by examiner

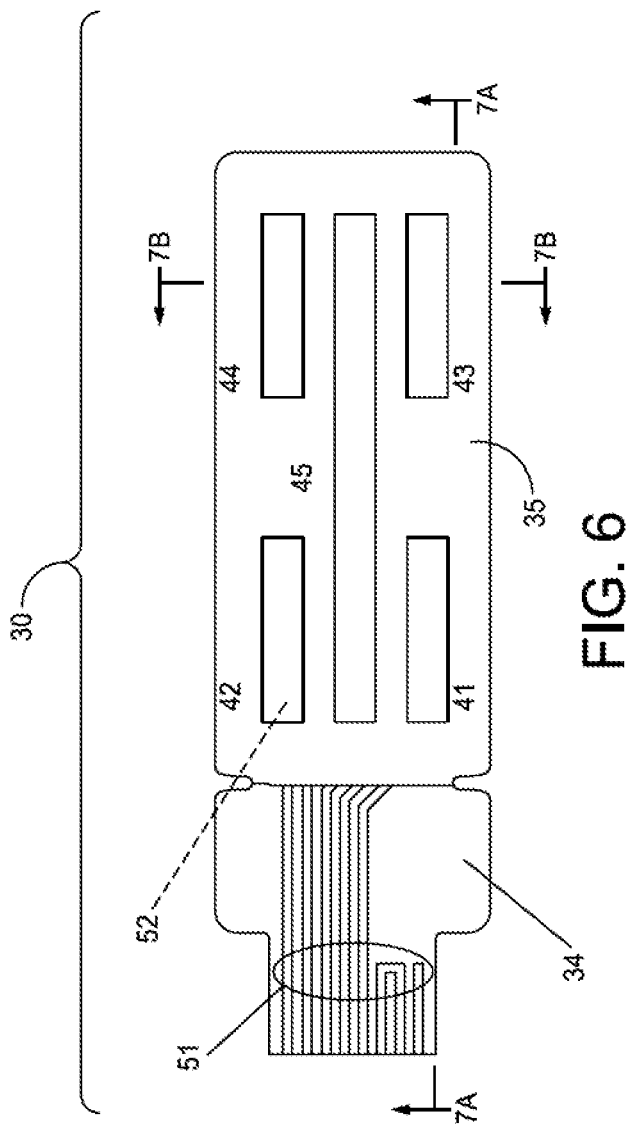
FIG. 6
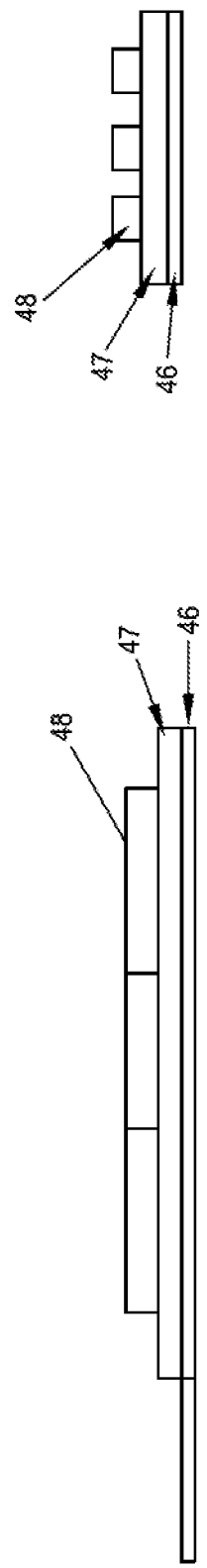
FIG. 6B
FIG. 6A

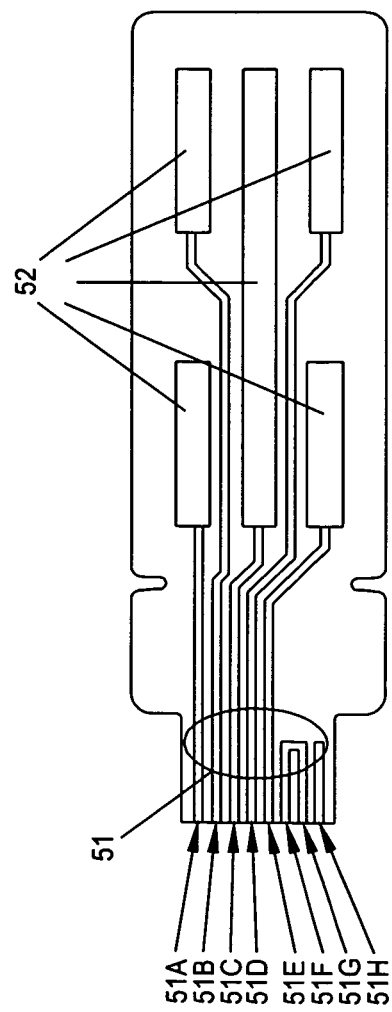
FIG. 7
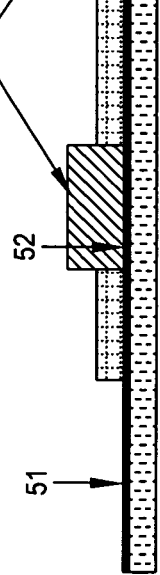
FIG. 7B
FIG. 7A

APPARATUS AND METHOD FOR THE AUTOMATED MEASUREMENT OF SURAL NERVE CONDUCTION VELOCITY AND AMPLITUDE

REFERENCE TO PENDING PRIOR PATENT APPLICATIONS

This patent application claims benefit of:
(i) prior U.S. Provisional Patent Application Ser. No. 61/403,453, filed Sep. 16, 2010 by Shai N. Gozani for NC-STAT® SL;
(ii) prior U.S. Provisional Patent Application Ser. No. 61/459,127, filed Dec. 6, 2010 by Shai N. Gozani for NC-STAT® SL;
(iii) prior U.S. Provisional Patent Application Ser. No. 61/467,857, filed Mar. 25, 2011 by Shai N. Gozani et al. for NC-STAT® SL;
(iv) prior U.S. Provisional Patent Application Ser. No. 61/516,944, filed Apr. 11, 2011 by Bonniejean Boettcher et al. for NC-STAT® SL; and
(v) prior U.S. Provisional Patent Application Ser. No. 61/571,203, filed Jun. 22, 2011 by Shai N. Gozani et al. for NC-STAT® DPNCHECK™.

The five (5) above-identified patent applications are hereby incorporated herein by reference.

FIELD OF THE INVENTION

This invention relates to apparatus and methods for the assessment of electrophysiological signals, and more particularly to the assessment of sural nerve conduction velocity and amplitude.

BACKGROUND OF THE INVENTION

Diabetes Mellitus ("DM") is a common disease involving ineffective regulation of blood glucose levels. There are over 25 million people in the United States with DM, and recent projections suggest that over 350 million people have the disease worldwide. There are two primary forms of DM. Type I DM generally affects children and young adults and is related to a primary deficiency of the insulin hormone. Type II DM usually affects adults, often over the age of 50, but increasingly in younger adults as well. It is a complex disease that generally starts as a resistance to insulin action that may progress to secondary insulin deficiency. The causes of Type I and Type II DM are not entirely known although genetic, environmental, and lifestyle risk factors have been identified.

Although acutely high or low blood glucose levels are dangerous, the primary sources of DM-associated morbidity and mortality are the long term macrovascular and microvascular complications of the disease. Macrovascular complications refer to cardiovascular events such as myocardial infarction ("heart attack") and stroke. Microvascular complications refer to pathological damage to the nerves, eyes, and kidneys of people with DM.

The most common microvascular complication of DM is neuropathy, or nerve damage. Diabetic neuropathy affects 60% or more of people with DM. Diabetic neuropathy may include damage to the large myelinated nerve fibers, the small myelinated and unmyelinated nerve fibers, and the autonomic nerves. The most common form of diabetic neuropathy is the large fiber form of the disease which is often termed diabetic peripheral neuropathy ("DPN"). DPN leads to pain and disability, and is the primary trigger for foot ulcers which may result in lower extremity amputations.

Because of the severe consequences of DPN, early detection of this complication of DM, and interventions to prevent or slow down progression of the neuropathy, are of paramount importance. Unfortunately, detection of DPN is challenging, particularly at its early stages when it may be most susceptible to intervention. Current methods of detecting and monitoring DPN range from clinical evaluation (including symptoms and signs obtained on simple physical examination) to various tests that include the 5.07/10-g monofilament test (where a column of "fishing line" is pressed into the foot of the patient, with the goal being for the patient to detect the contact before the column of "fishing line" bends), the tuning fork test (where a vibrating tuning fork is placed against the big toe of the patient, with the goal being for the patient to detect the vibration of the tuning fork), and quantitative vibration perception testing (where electronics are used to measure the magnitude of a vibration detectable by the patient). While all of these methods have utility, they are subjective, have inadequate sensitivity or specificity, or both, and have poor reproducibility. The "gold standard" method for evaluation of DPN is a nerve conduction study. In a nerve conduction study, a nerve is electrically stimulated at a first location along the nerve, and then the electrical response of the nerve is detected at a second location along the nerve. Among other things, the rate at which the nerve conducts the signal ("the nerve conduction velocity") and the magnitude of the evoked signal ("the amplitude") are reliable indicators of neuropathy. Unlike the aforementioned techniques, nerve conduction testing is objective, sensitive, specific, and reproducible. As a result, most clinical guidelines suggest confirmation of DPN by nerve conduction testing for a reliable diagnosis.

Despite its technical and clinical attributes, nerve conduction testing is not currently widely used in the detection and monitoring of DPN. The reasons for this include the limited availability, complexity and high cost of the study when performed by specialists, usually a neurologist, using traditional electrodiagnostic equipment. To overcome these obstacles to adoption, a number of devices have been developed to simplify and increase access to nerve conduction studies through automation and other techniques. For example, devices that perform nerve conduction measurements using pre-fabricated, nerve-specific electrode arrays have been developed that largely automate the required technical steps of a nerve conduction study (see, for example, U.S. Pat. No. 5,851,191 issued to Gozani et al. and U.S. Pat. No. 7,917,201 issued to Gozani et al.). Another related solution found in the prior art (see U.S. Pat. No. 5,215,100 issued to Spitz et al.) is an apparatus for the assessment of Carpal Tunnel Syndrome (CTS) in which all the electrodes required to stimulate and record from the nerve are fixed by the device.

These prior art solutions suffer from a number of deficiencies. All devices described in the prior art are either general purpose (i.e., multi-nerve, multi-application) nerve conduction testing devices or they are designed specifically for evaluation of the median nerve for the assessment of CTS. General purpose devices, of necessity, must adapt to the various anatomical and electrophysiological aspects of many different nerves. As a result, only limited customization is possible and the onus remains on the user of the general purpose device to address the sources of variations—such as through the placement of individual electrodes or even pre-configured electrode arrays. As a result, despite simplifying nerve conduction measurements relative to the traditional approaches, the general purpose testing devices still require a fair amount of training in order to properly perform the nerve conduction test procedures. Also, those devices in the prior art specifically designed for the evaluation of the median nerve have little relevance to the requirements of the present invention, which is the assessment of the sural nerve. The primary reason for this is that the anatomy and electrophysiology of the sural nerve (used for the assessment of DPN) is substantially different from that of the median nerve (used for the assessment of CTS). Therefore devices specifically designed for testing of the median nerve cannot be used to test the sural nerve. Another issue with general purpose testing devices is that they require two discrete components—a device with the electronic circuits needed to perform a nerve conduction test, and a nerve-specific electrode array which provides an interface between the unique characteristics of the particular nerve being tested and the common testing device. This two-component requirement limits attempts to reduce test costs, particularly because it restricts the ability to reduce the size of the electrode array, which is a primary cost driver in nerve conduction testing.

SUMMARY OF THE INVENTION

The present invention is a fully-integrated, hand-held sural nerve conduction testing device. The sural nerve is a sensory-only nerve located in the lower calf and ankle region of the body. Sural nerve conduction is a standard and quantitative biomarker of DPN. Sural nerve conduction testing detects DPN with high diagnostic sensitivity and reveals abnormalities before there is clinical evidence of neuropathy. Sural nerve conduction is correlated to the morphological severity of myelinated fiber loss and is therefore predictive of foot ulcer risk.

The purpose of this new device is to easily, rapidly, and accurately measure and report two common sural nerve conduction parameters: the onset conduction velocity (hereafter abbreviated as "CV") and the sensory response amplitude (hereafter described as "amplitude"). The term "fully-integrated" indicates that all of the components needed for performing a nerve conduction test of the sural nerve are incorporated into a single physical unit, as opposed two or more distinct components (for example, an electrode array and a testing instrument connected by a cable). The term "hand-held" indicates that the device is applied to the patient by a qualified user in order to test the nerve, rather than being a fixed apparatus into which the patient places their limb. The "fully-integrated" and "hand-held" characteristics require technological advances that are both novel and non-obvious.

The present invention addresses the deficiencies of the prior art. First, the current device is designed and optimized for testing of the sural nerve. As a result, the test procedure has been substantially simplified and automated to the point where it can be taught to someone in 30-60 minutes after which they should be able to obtain accurate sural nerve conduction results. Further, due to its focused application on the sural nerve, the test procedure has been automated to the point where the test duration is typically only 15-30 seconds in length. Another benefit of its focused application on the sural nerve is that the cost of both the hardware and disposable components have been substantially reduced relative to the general purpose devices described in the prior art.

In one preferred form of the present invention, there is provided apparatus for measuring sural nerve conduction velocity and amplitude, the apparatus comprising:
a housing;
stimulation means mounted to the housing for electrically stimulating a human sural nerve;
a biosensor releasably mounted to the housing, the biosensor comprising a plurality of electrodes for detecting a sural nerve response evoked by the stimulation means;
acquisition means mounted to the housing and electrically connected to the biosensor for electrically acquiring the sural nerve response detected by the biosensor;
processing means mounted to the housing and electrically connected to the acquisition means for digitizing, processing and storing the acquired sural nerve response;
calculation means mounted to the housing and electrically connected to the processing means for calculating the conduction velocity and amplitude of the processed sural nerve response; and
display means mounted to the housing for displaying the sural nerve conduction velocity and amplitude;
wherein the stimulation means and the biosensor are designed to be placed on a patient's anatomy, in the vicinity of a sural nerve, by manipulating the housing.

In another preferred form of the present invention, there is provided apparatus for measuring sural nerve conduction velocity and amplitude, the apparatus comprising:
a housing;
stimulation means mounted to the housing for electrically stimulating a human sural nerve;
a seat on the housing for releasably mounting a biosensor to the housing, wherein the biosensor is of the type comprising a plurality of electrodes for detecting a sural nerve response evoked by the stimulation means;
acquisition means mounted to the housing for electrical connection to a biosensor mounted on the seat and for electrically acquiring the sural nerve response detected by the biosensor;
processing means mounted to the housing and electrically connected to the acquisition means for digitizing, processing and storing the acquired sural nerve response;
calculation means mounted to the housing and electrically connected to the processing means for calculating the conduction velocity and amplitude of the processed sural nerve response; and
display means mounted to the housing for displaying the sural nerve conduction velocity and amplitude;
wherein the stimulation means and a biosensor releasably mounted on the seat are designed to be placed on a patient's anatomy, in the vicinity of a sural nerve, by manipulating the housing.

In another preferred form of the present invention, there is provided apparatus for measuring sural nerve conduction velocity and amplitude, the apparatus comprising:
a biosensor adapted to be releasably mounted to the housing of a nerve conduction testing device so that the biosensor moves in conjunction with the housing, the biosensor comprising a plurality of electrodes for detecting a sural nerve response evoked by the nerve conduction testing device and an electrical connector for electrically connecting the plurality of electrodes to the nerve conduction testing device.

In another preferred form of the present invention, there is provided a method for measuring sural nerve conduction velocity and amplitude, the method comprising:
releasably mounting a biosensor to the housing of a nerve conduction testing device so that the biosensor moves in conjunction with the housing;
positioning the housing of the nerve conduction testing device so that the nerve conduction testing device is positioned to electrically stimulate a human sural nerve and the biosensor is positioned to detect a sural nerve response evoked by the stimulation means;
using the nerve conduction testing device to electrically stimulate a sural nerve and to acquire the sural nerve response detected by the biosensor; and processing the acquired sural nerve response to determine the conduction velocity and amplitude of the processed sural nerve response.

In another preferred form of the present invention, there is provided a fully-integrated, hand-held nerve conduction testing apparatus comprising a hand-held component and a single-patient use biosensor, wherein the biosensor is both physically and electrically connected to the hand-held component to acquire a nerve response.

In another preferred form of the present invention, there is provided a biosensor for detecting a nerve response, the biosensor comprising:
  a substrate;
  a plurality of electrodes mounted to the substrate for detecting the nerve response; and
  a biosensor reuse code carried by the substrate for determining reuse of the biosensor, wherein the biosensor reuse code is randomly assigned to that biosensor.

In another preferred form of the present invention, there is provided a kit comprising:
  a plurality of biosensors for detecting nerve responses, wherein each of the biosensors comprises a substrate, a plurality of electrodes mounted to the substrate for detecting a nerve response, and a biosensor reuse code carried by the substrate for determining reuse of the biosensor;
  wherein the biosensor reuse code varies randomly among the biosensors in the kit.

In another preferred form of the present invention, there is provided a method for determining the reuse of a biosensor in connection with a test machine, the method comprising the steps of:
  connecting a biosensor to the test machine, wherein the biosensor comprises a biosensor reuse code randomly assigned to that biosensor;
  identifying the biosensor reuse code associated with the connected biosensor;
  comparing the identified biosensor reuse code with the biosensor reuse codes associated with the biosensors previously connected to the test machine; and
  determining that the biosensor has been reused if the comparison indicates that the identified biosensor reuse code and the codes from the previously connected biosensors form a pattern that is unlikely from a random distribution of biosensor reuse codes, or determining that the biosensor has not been reused if the aforementioned pattern is likely from a random distribution of biosensor reuse codes.

In another preferred form of the present invention, there is provided a method for preventing the reuse of a biosensor in connection with a test machine, the method comprising the steps of:
  connecting a biosensor to the test machine, wherein the biosensor comprises a biosensor reuse code randomly assigned to that biosensor;
  identifying the biosensor reuse code associated with the connected biosensor;
  comparing the identified biosensor reuse code with the biosensor reuse codes associated with the biosensors previously connected to the test machine; and
  allowing the test to proceed if the comparison indicates that the identified biosensor reuse code is part of a random distribution of biosensor reuse codes, or preventing the test from proceeding if the comparison indicates that the identified biosensor reuse code is not part of a random distribution of biosensor reuse codes.

In another preferred form of the present invention, there is provided an adapter for connecting a biosensor to a testing device, the adapter comprising a biosensor reuse code carried by the adapter for determining reuse of the biosensor, wherein the biosensor reuse code is presented by the adapter to the testing device.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 6 is a schematic view of the top of the biosensor;

FIG. 6A is a schematic side view of the biosensor shown in FIG. 6;

FIG. 6B is a schematic end view of the biosensor shown in FIG. 6;

FIG. 7 is another schematic view of the top of the biosensor shown in FIG. 6;

FIG. 7A is a schematic cross-sectional view taken along line 7A-7A of FIG. 6;

FIG. 7B is a schematic cross-sectional view taken along line 7B-7B of FIG. 6;

DETAILED DESCRIPTION OF THE PREFERRED EMBODIMENTS

Device Description

Figure 1:
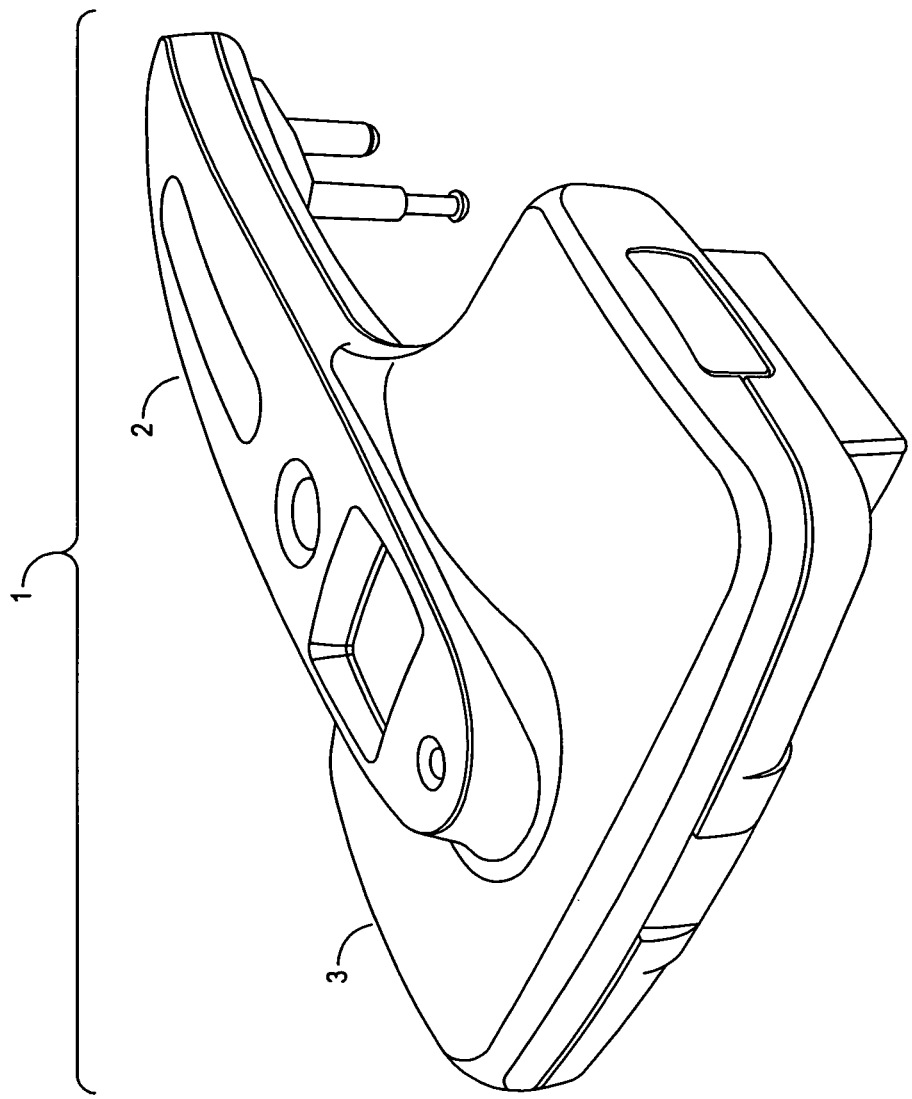
FIG. 1 is a schematic view of a novel, fully-integrated, hand-held sural nerve conduction testing device formed in accordance with the present invention.

The present invention is a fully-integrated, hand-held sural nerve conduction testing device. The device is designed exclusively for non-invasive nerve conduction measurements of the human sural nerve in the region of the lower calf and ankle. The sural nerve is an almost-entirely sensory nerve formed from the merger of the medial and lateral sural cutaneous nerves which are branches of the tibial and common fibular nerves (which are themselves branches of the sciatic nerve). After forming at the distal third of the gastroc muscle, the sural nerve runs down the leg on the posterior-lateral side, then posterior to the lateral malleolus where it runs deep to the fibularis tendon sheath and reaches the lateral tuberosity of the fifth toe, where it ramifies. The sural nerve transmits sensory signals from the posterior lateral corner of the leg, the lateral foot and the 5th toe.

Sural nerve conduction is a standard and quantitative biomarker of DPN. Sural nerve conduction testing detects DPN with high diagnostic sensitivity and reveals abnormalities before there is clinical evidence of neuropathy. Sural nerve conduction is correlated to the morphological severity of myelinated fiber loss and is therefore predictive of foot ulcer risk.

There are a variety of nerve conduction methodologies by which the sural nerve can be evaluated. For example, the nerve can be tested orthodromically by stimulating the nerve at the ankle and then measuring the nerve response after it has conducted a known distance up the calf, or the nerve can be tested antidromically by stimulating the nerve in the calf and then measuring the nerve response after it has conducted a known distance to the ankle. Another methodological factor in nerve conduction testing for the sural nerve includes the distance between the points of stimulation and recording, which generally varies from about 8 cm to 16 cm. Another methodological factor associated with nerve conduction testing of the sural nerve is the configuration of the recording electrodes, including their shape, size, and the distance between them. In the preferred embodiment of the present invention, the sural nerve is tested orthodromically with a stimulation-to-recording distance of 9.22 cm. The preferred recording electrode configuration is provided below in the description of the biosensor.

The purpose of the present invention is to easily, rapidly, and accurately measure and report two common sural nerve conduction parameters: the onset conduction velocity (hereafter abbreviated as "CV") and the sensory response amplitude (hereafter described as "amplitude"). The term "fully-integrated" indicates that all of the components needed for performing a nerve conduction test of the sural nerve are incorporated into a single physical unit, as opposed two or more distinct components (for example, an electrode array and a testing instrument connected by a cable). The term "hand-held" indicates that the device is applied to the patient by a qualified user in order to test the nerve, rather than being a fixed apparatus into which the patient places their limb. The "fully-integrated" and "hand-held" characteristics require technological advances that are both novel and non-obvious.

An overall view of the present invention is provided in FIG. 1. As shown, the invention comprises a single fully-integrated, hand-held device 1 with a narrow handle 2 and a head 3. In the preferred embodiment, device 1 is 19.0 cm in length and 11.5 cm in width at its widest point on head 3. The most critical dimension is the distance between cathode 10 (FIG. 3) of device 1 (which is the point of nerve stimulation) and the center of the electrodes 41, 43 on the biosensor 30. When biosensor 30 is seated in the biosensor port 16 (FIG. 3), electrodes 41, 43 are closest to cathode 10. That distance (i.e., the distance between cathode 10 and electrodes 41, 43) represents the conduction distance between the point of nerve stimulation via cathode 10 and arrival of the evoked nerve impulse at electrodes 41, 43. This distance is 9.22 cm in the preferred construction and is used to calculate the CV as will be described below.

Figure 2:
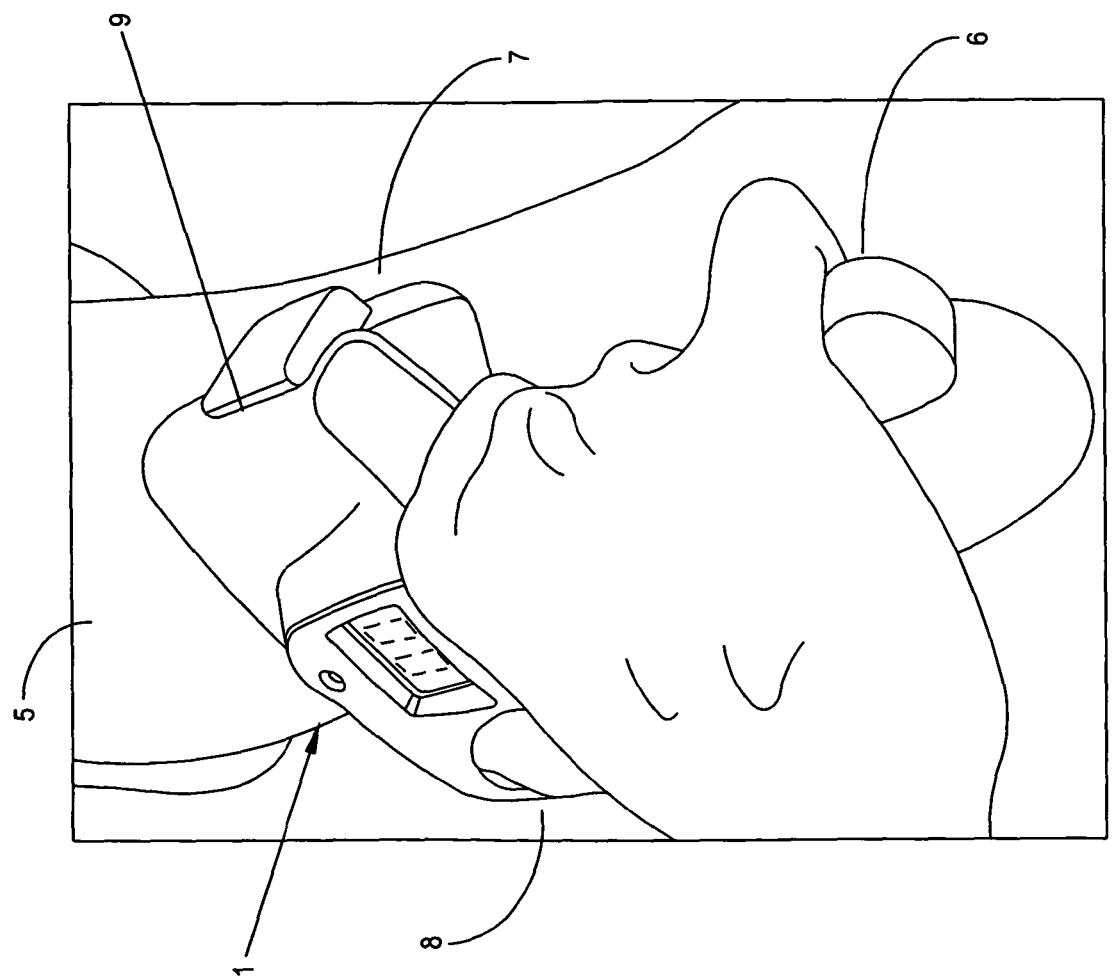
FIG. 2 is a schematic view showing the testing device of FIG. 1 being placed on a patient's limb.

A preferred use of the invention is shown in FIG. 2. As shown, device 1 is placed against the lateral aspect of the patient's lower leg 5 such that (i) the stimulation probes 10, 11 (FIG. 3) mechanically contact the leg immediately behind the outside ankle bone ("lateral malleoulus") 6, and (ii) biosensor 30 contacts the patient's lower calf 7, with the inner edge (one of the two sides 8 or 9, depending on the limb) of device 1 being approximately aligned with the Achilles tendon. In order to reliably measure nerve conduction of the sural nerve, device 1 must have enough degrees of freedom in order to conform to the patient's lower leg anatomy and thereby allow for robust and stable contact of certain device components (i.e., the stimulating electrodes and the detecting electrodes) with the patient. The means to accomplish this robust electrical contact are described in detail below.

Figure 3:
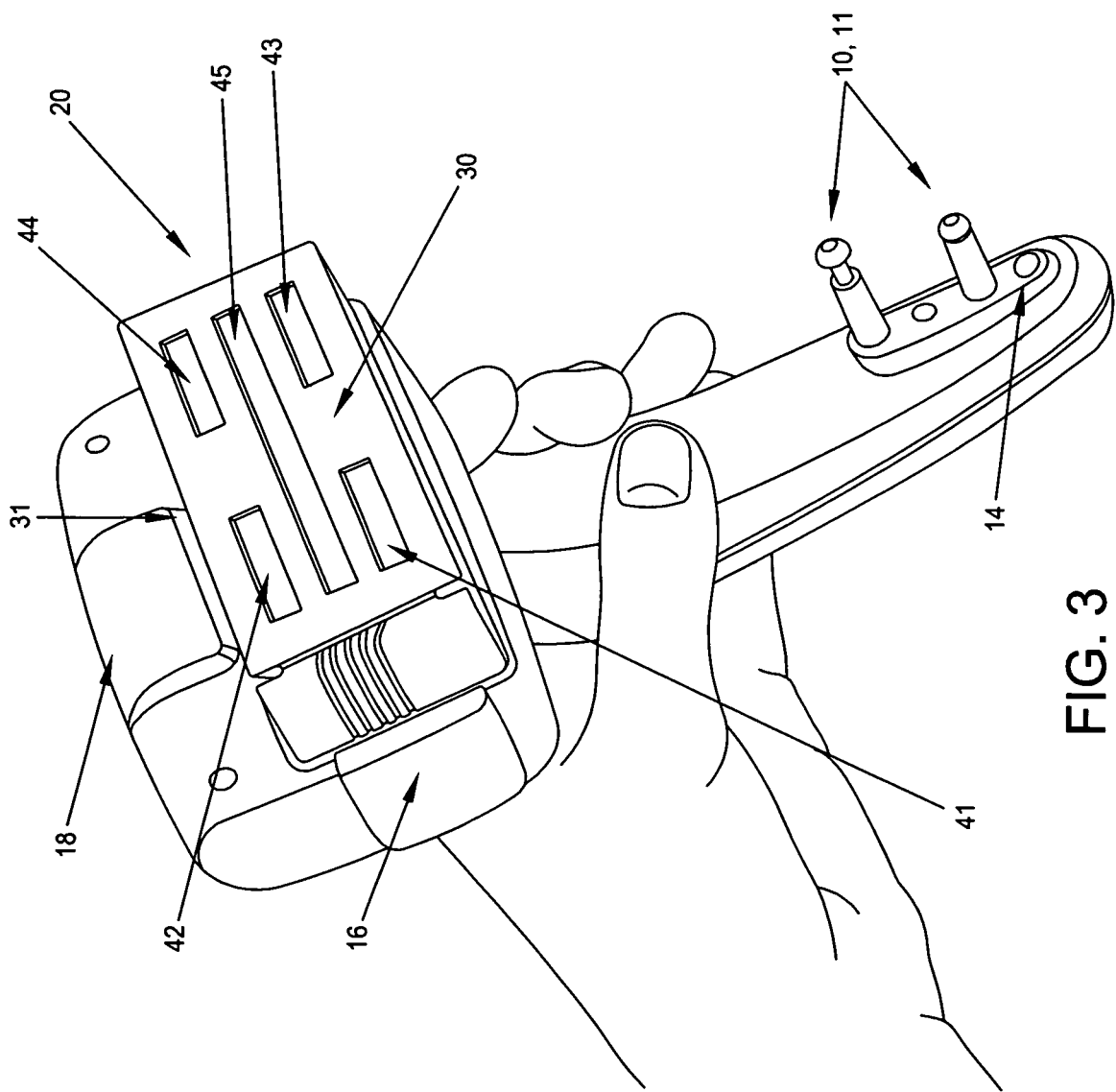
FIG. 3 is a schematic view of the bottom of the testing device shown in FIG. 1.

FIG. 3 is a bottom view of the preferred embodiment of device 1. This view shows the surfaces that contact the patient. There are two stainless steel probes 10, 11 for electrically stimulating the sural nerve when device 1 is placed against the patient in the manner shown in FIG. 2. The cathode 10 has a variable height relative to handle 2 due to its spring-loaded construction. In the preferred embodiment this variable height ranges from 2.5 cm (compressed condition) to 3.3 cm (uncompressed condition) from handle 2. The anode 11 preferably has a fixed height relative to handle 2, which in the preferred embodiment is fixed at 2.3 cm from the handle. The variable length cathode 10 is novel inasmuch as it provides a degree of freedom to enable robust contact of both stimulating probes 10, 11 with the patient anatomy in the vicinity of the ankle, which is non-planar and has a topology which varies from patient to patient. Although it is possible to electrically stimulate the sural nerve through the stimulating probes 10, 11 by direct contact with the patient's skin, it is preferable to use a small amount of conductive hydrogel on the outer tip of each probe so as to reduce the impedance of the probe-skin interface.

Figure 3A:
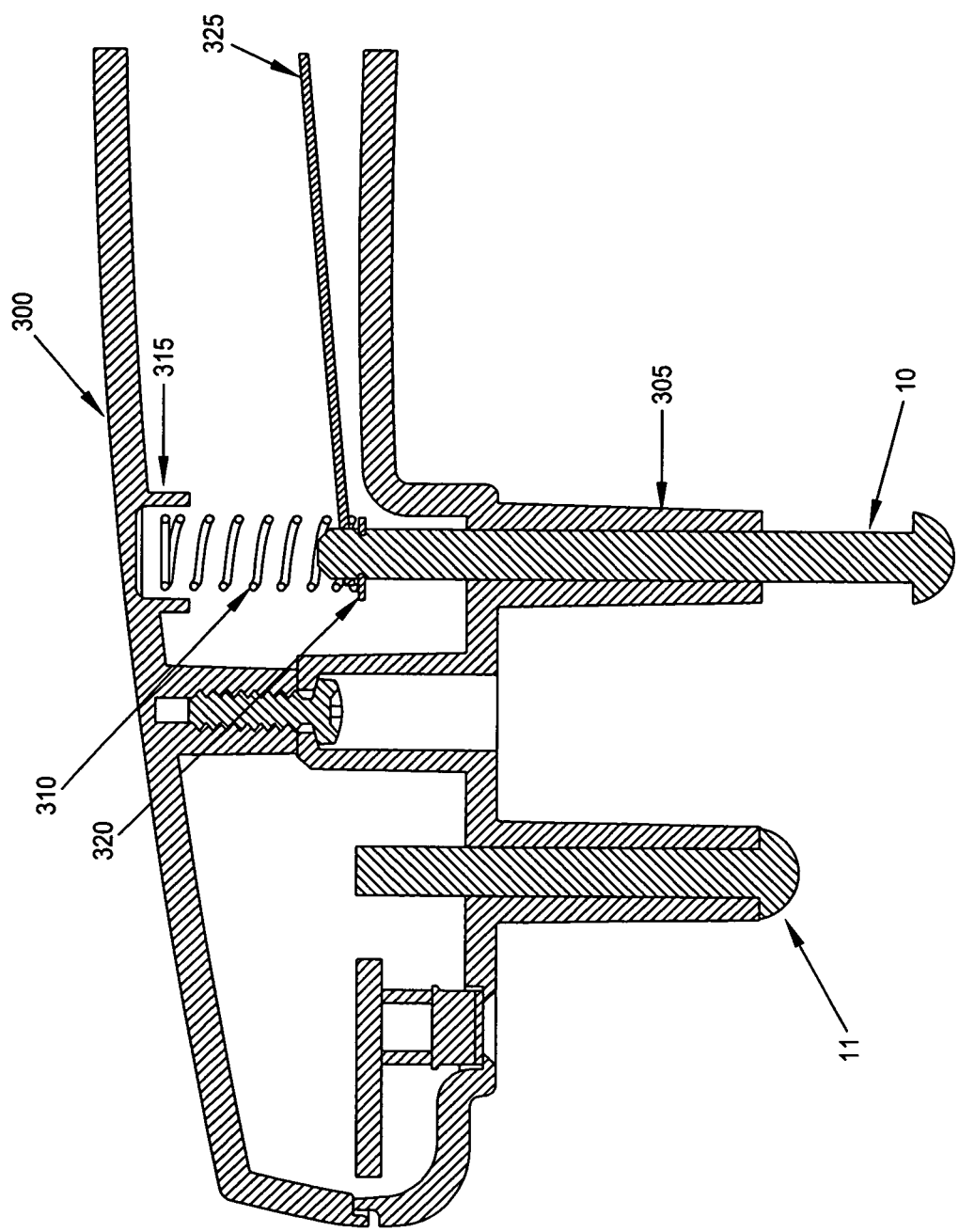
FIGS. 3A and 3B are schematic sectional views showing the preferred construction details for the spring-loaded cathode of the testing device shown in FIG. 1.
Figure 3B:
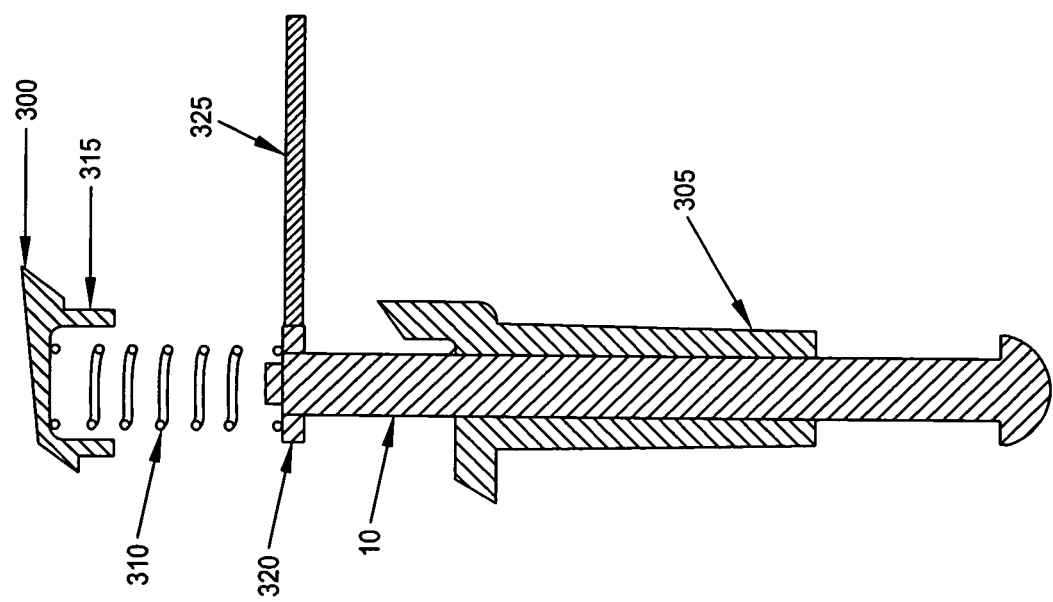

FIGS. 3A and 3B show one preferred construction for the spring-loaded cathode 10. More particularly, in this form of the invention, device 1 comprises a plastic enclosure 300 which forms the body of device 1, with plastic enclosure 300 comprising a tubular projection 305 for slidably receiving cathode 10 therein. A spring 310 is captured between the proximal end of cathode 10 and a seat 315 formed on plastic enclosure 300. A fastener 320 may be used to secure spring 310 to the proximal end of cathode 10 if desired. A flexible cable 325 electrically connects cathode 10 to the stimulation source. Also shown in FIGS. 3A and 3B is the fixed anode 11.

Device 1 includes an infra-red thermometer 14 (FIG. 3) for non-contact measurement of the patient's skin surface temperature in the vicinity of the ankle bone. As will be discussed below, this temperature measurement is used to compensate for the effects of temperature on nerve conduction results. The use of a non-contact temperature measuring device is an important aspect of the present invention, since it permits reliable temperature measurements to be made in the irregular skin surface topology associated with the sural nerve.

Figure 4:
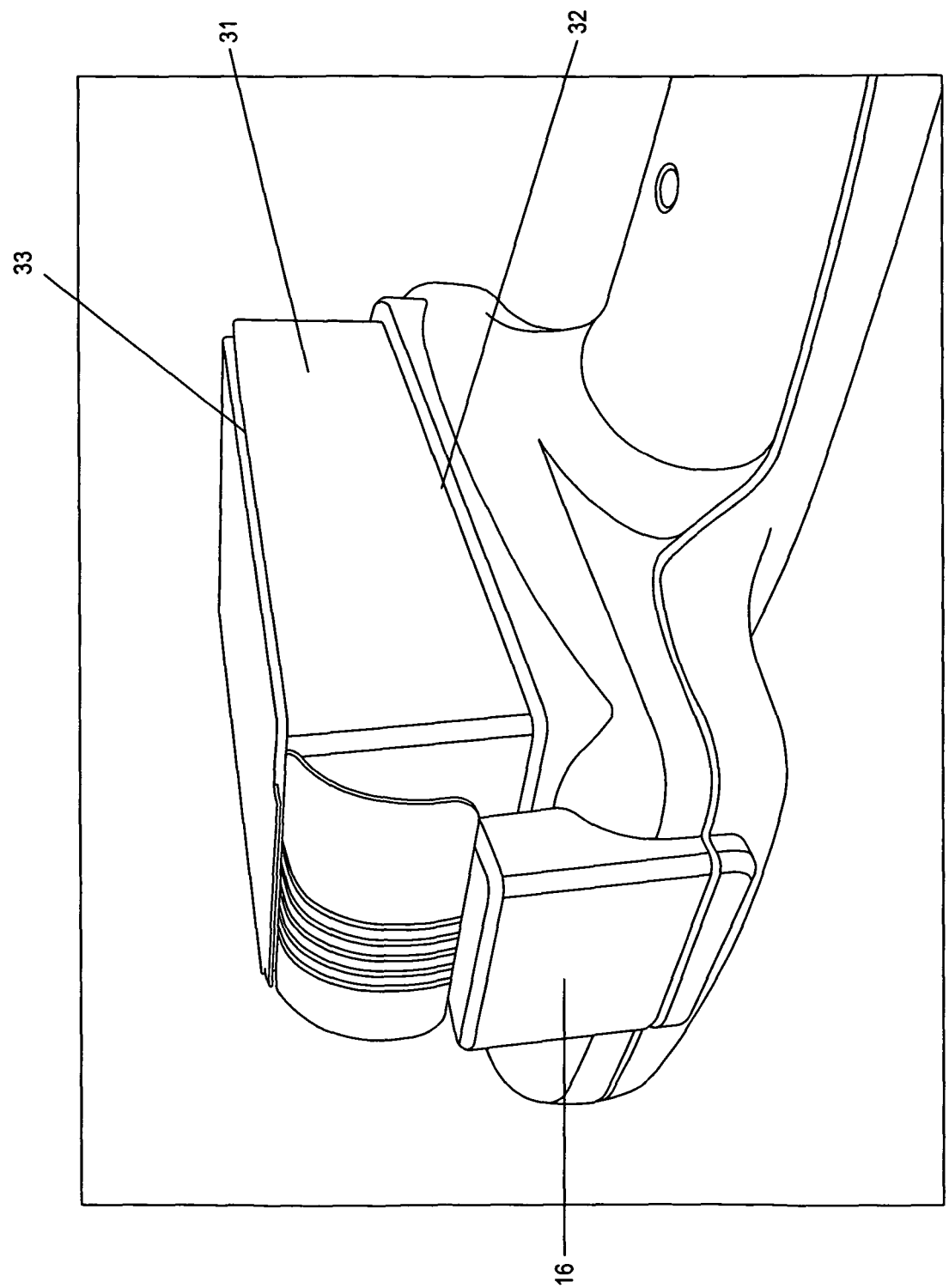
FIG. 4 is a schematic view showing selected portions of the testing device of FIG. 1, including the biosensor, foam pad, and device head.

Head 3 of device 1 supports biosensor 30, which provides a bioelectrical interface to the patient. Biosensor 30, which is described in detail below, is disposable and should be replaced between patients. Biosensor 30 is secured to device 1 by a foam pad 31 (FIGS. 3 and 4) which is provided with non-permanent adhesive on both sides of the foam pad—the adhesive on the inner surface of foam pad 31 releasably secures the foam pad to head 3 of device 1, and the adhesive on the outer surface of foam pad 31 releasably secures biosensor 30 to the foam pad. Foam pad 31 is disposable but may be used for multiple patients as it does not come in direct contact with the patient. Foam pad 31 is shown in greater detail in FIG. 4. One side 32 of the foam pad attaches to the bottom surface of head 3 of device 1, and the other side 33 attaches to the non-patient contact side of biosensor 30. In the preferred embodiment, foam pad 31 is 2.2 cm thick. Although various types of foam may be used, in the preferred embodiment, polyurethane foam is used. When device 1 is pressed against the patient's leg as shown in FIG. 2, the foam pad provides multiple degrees of freedom by which biosensor 30 may conform to the patient's anatomy so as to establish complete contact with the patient's skin. A uniform and complete contact between electrodes 41, 42, 43, 44 and 45 (FIG. 3) and patient skin makes it possible to acquire high quality nerve conduction signals over a wide variety of patient anatomy. The use of foam pad 31 in achieving a uniform and complete contact of electrodes and patient skin is novel and non-obvious. Biosensor 30 is connected to the internal electronics of device 1 via biosensor port 16.

Thus it will be seen that device 1 includes (i) novel means for ensuring reliable electrical contact between the stimulating electrodes and the skin of the patient (i.e., the spring-loaded cathode 10 and the fixed-position anode 11), and (ii) novel means for ensuring reliable electrical contact between the detecting electrodes and the skin of the patient (i.e., the use of foam pad 31 to support biosensor 30).

Head 3 of device 1 includes a battery compartment 18 (FIG. 3) with a removable door for replacement of the battery 109 (FIG. 8), which in the preferred embodiment is a widely available 3V Lithium Ion battery (CR123A). A mini USB port 20 (FIG. 3) allows for device 1 to communicate with external devices (such as a PC) using the standard USB protocol.

Figure 5:
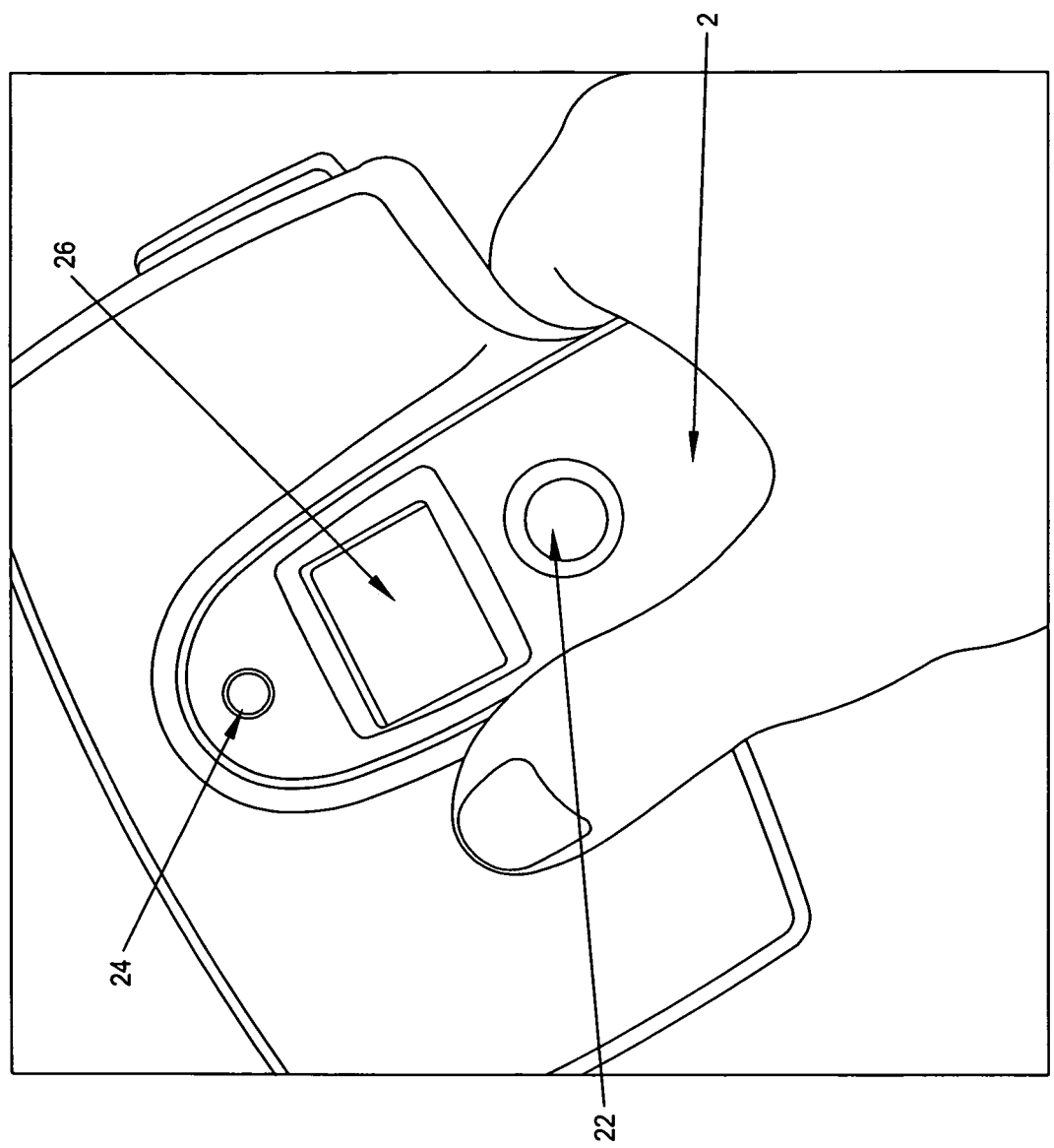
FIG. 5 is a schematic view of the top of the testing device shown in FIG. 1.
Figure 7C:
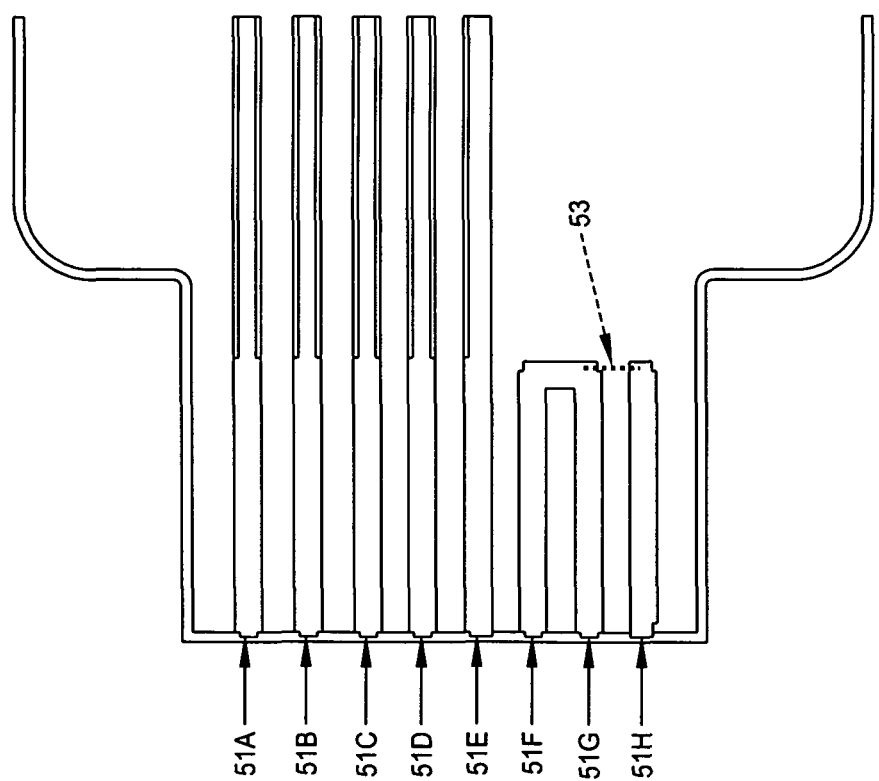
FIG. 7C is an enlarged schematic view of selected portions of the traces of the biosensor shown in FIG. 6.

FIG. 5 shows the top of device 1, which provides the user interface. In the preferred embodiment, the user interface consists of one push-button switch 22, an LED 24, and an LCD 26. Push-button switch 22 turns on device 1 if the device is powered off. If device 1 is powered on, then switch 22 initiates a nerve conduction test. LED 24 has three colors (green, amber, and red) and is used to indicate device status, which may include green to represent "ready to test," amber to indicate "battery low," and red to indicate "error—cannot perform test." In the preferred embodiment, LCD 26 is a two 7-segment display with additional dot indicators. LCD 26 displays the results of the sural nerve conduction test or an error status 180 (see FIG. 12) to the user. A successful test is accompanied by a toggling display on the LCD of (i) the numerical values of the CV, and (ii) the amplitude of the nerve response (or an amplitude of 0, without a CV, to indicate that sural nerve conduction is not detectable). An unsuccessful test is accompanied by an error status message 180 (see FIG. 12) on LCD 26 which indicates the probable cause for the failure. In the preferred embodiment, the error status messages include "Sn" for an error related to the biosensor, "Er" for an error related to excessive muscle interference, "Pr" for an error related to stimulating probes, and "° C." for an error related to patient skin surface temperature.

Biosensor Description

A preferred embodiment of biosensor 30 is shown in FIGS. 6, 6A, 6B, 7, 7A and 7B. Biosensor 30 is a multi-layer construct of mylar 46, Ag (silver) traces 51, Ag—AgCl pads 52, foam 47, and hydrogels 48. Biosensor 30 also comprises a patient contact area 35 and a device connection tail 34 (FIG. 6). Patient contact area 35 preferably has a width 8.77 cm and a height 3.77 cm. Tail 34 electrically connects biosensor 30 to device 1 via biosensor port 16. Biosensor 30 consists of 5 discrete electrodes 41, 42, 43, 44, 45 that are comprised of hydrogel layered on top of an Ag—AgCl pad. The four smaller electrodes (41, 42, 43 and 44) are electrically connected to the differential inputs of instrumentation amplifiers (see below) and therefore function as "active" electrodes. The single long electrode 45 is connected to the reference input of the instrumentation amplifiers and therefore functions as a "reference" electrode. In the preferred embodiment of biosensor 30, the electrodes are connected so as to form two distinct sural nerve response recording channels. In particular, electrodes 41 and 42 comprise one recording channel, and electrodes 43 and 44 comprise a second distinct recording channel. Alternative embodiments of the present invention include biosensors comprised of only one recording channel, or biosensors comprised of three or more recording channels. Alternative configurations of reference electrode 45 include multiple distinct reference electrodes rather than a single common reference electrode.

In the preferred embodiment shown in FIG. 6, the active recording electrodes 41, 42, 43 and 44 each have dimensions of 2.5 cm by 0.5 cm, and the reference electrode 45 has dimensions 0.5 cm by 7.0 cm. The two active electrodes comprising each recording channel (i.e., 41, 42 and 43, 44) are preferably separated by a distance of 2.0 cm measured center to center. The reference electrode 45 is preferably separated by 1.0 cm from each of the active electrodes 41, 42, 43, 44 measured center to center.

Tail 34 of biosensor 30 provides an electrical connection between device 1 and biosensor 30 via biosensor port 16. Tail 34 is the male connector, and biosensor port 16 is the female connector. In the preferred form of the invention, tail 34 comprises 8 parallel traces 51. Five of the traces (51A, 51B, 51C, 51D and 51E) connect electrodes 41, 42, 43, 44, 45, respectively, to the corresponding inputs on the aforementioned instrumentation amplifiers. Two of the traces (51F and 51G) are connected together such that when tail 34 of biosensor 30 is inserted into biosensor port 16 of device 1, an electrical circuit is closed. This closed circuit allows device 1 to detect and thereby confirm that biosensor 30 is connected to device 1. Confirmation is indicated to the user by a steady green color on LED 24. One trace (51H) represents a 1-bit biosensor code which is used by the device software to determine whether biosensors 30 are being reused on multiple patients. The bit is coded as 0 or 1, depending on whether that trace (51H) is connected (e.g., via a connector 53, see FIG. 7C) to one of the other traces (51F, 51G), which is connected to ground upon insertion of tail 34 into device 1. It is intended that the 1-bit biosensor code associated with a given biosensor be randomly distributed, i.e., one-half of all biosensors 30 are intended to have a "0" 1-bit biosensor code, and one-half of all biosensors 30 are intended to have a "1" 1-bit biosensor code. The manner in which this 1-bit biosensor code is used to detect biosensor reuse is discussed below in the software description.

Hardware Description

Figure 8:
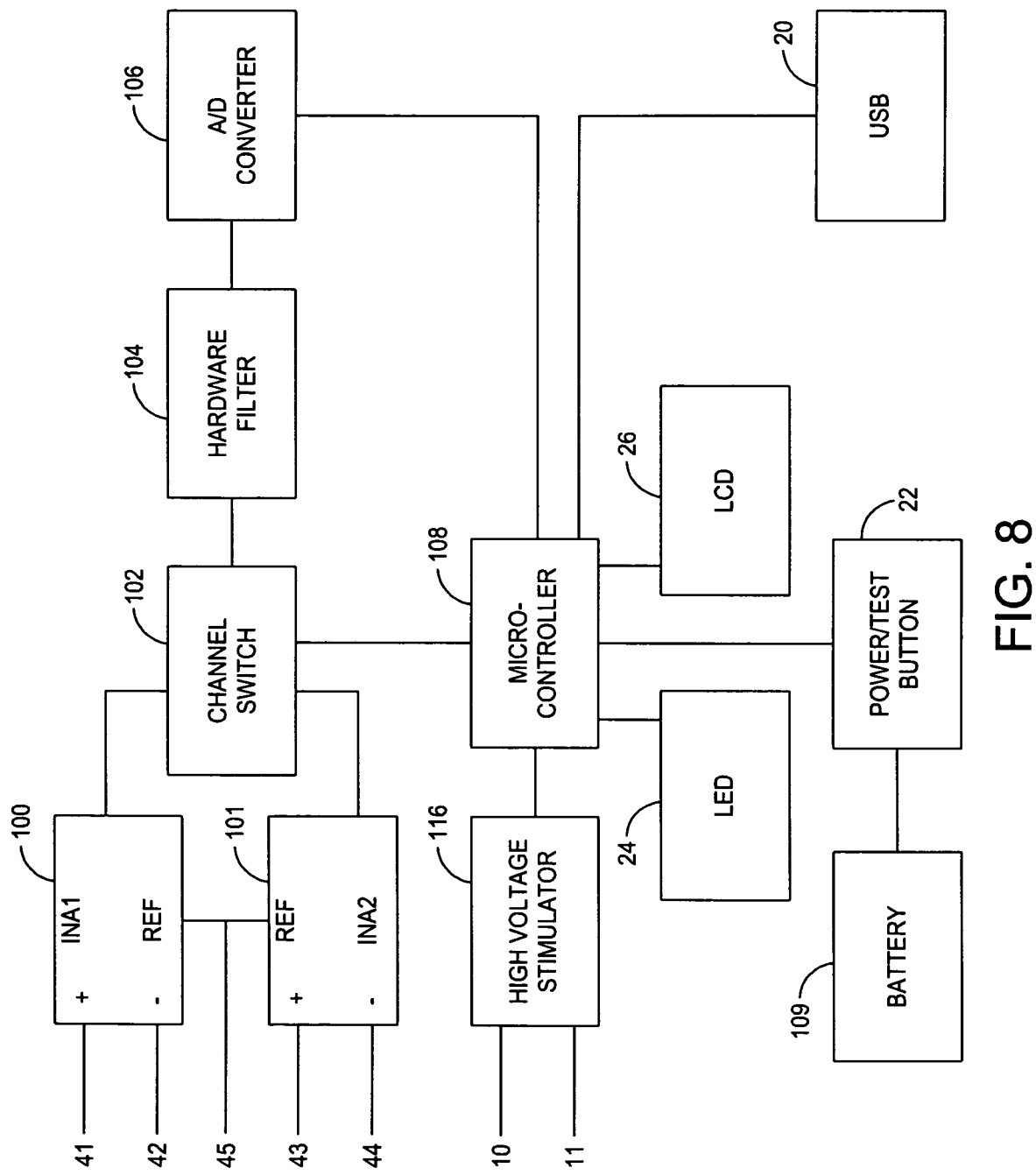
FIG. 8 is a high level hardware schematic of the testing device shown in FIG. 1.

FIG. 8 is a block diagram of a preferred embodiment of the internal electronics (hardware) of device 1. The hardware consists of two instrumentation amplifiers (INA) 100, 101 with differential inputs coming from the two pairs of active electrodes 41, 42 and 43, 44. In the preferred embodiment, these INAs have a typical input impedance $\geq 10^{10}$ (10 to the $10^{th}$ power) Ohms and a common mode rejection ratio 90 dB. The INAs 100, 101 share a common reference input coming from reference electrode 45. The outputs of INAs 100, 101 are fed into a 2×1 switch 102 that determines which of the two channels will be acquired and processed. Switch 102 is controlled by the microcontroller 108, with the channel selection determined by the test control software (see below). The channel selection may be different at different stages of the testing. The output of switch 102 is input into a band-pass filter 104. In the preferred embodiment, band-pass filter 104 has a low frequency cutoff of 2 Hz and a high frequency cutoff of 4900 Hz. The output of band-pass filter 104 is then digitized by the A/D converter 106, with the digital output going into the microcontroller 108 for storage and processing.

Microcontroller 108 triggers the high voltage stimulator 116 to deliver nerve stimulation to the patient via cathode 10 and anode 11. In a preferred embodiment, the high voltage stimulator 116 is a constant current stimulator that generates a monophasic square DC pulse with a duration of 50 to 100 μsecs. The output voltage of the high voltage stimulator is 400-440 V, with a typical value of 420 V. The high voltage stimulator is capable of delivering up to 100 mA into a 3.3 kOhm load.

Microcontroller 108 controls the user interface components including LED 24, LCD 26, and power/test button 22. Microcontroller 108 also communicates with an isolated USB port 20 (FIG. 3) for external communication (such as with a PC). The internal electronics of device 1 are powered from a single battery 109. In the preferred embodiment, this is the commonly-available 3V Lithium battery CR123A.

Principles of Operation

A nerve conduction test is performed on the patient by placing device 1 against the patient in the manner shown in FIG. 2 and described above. When in this disposition, cathode 10 is located over the sural nerve as the sural nerve passes behind the lateral malleoulus 6 (FIG. 2), and biosensor 30 is located over (or in a worst case, adjacent to) the sural nerve as the sural nerve approaches the Achilles tendon, about 9 cm from cathode 10. An important object of the present invention is that device 1 automatically adapts to testing either the left leg or the right leg of the patient. This "limb independence" is achieved because when device 1 is placed on the patient as described above, one of the two electrode pairs 41, 42 or 43, 44 of biosensor 30 will overlie (or lie immediately adjacent to) the patient's sural nerve. The appropriate electrode pair (i.e., 41, 42 or 43, 44) will be the electrode pair which is closest to the Achilles tendon because the sural nerve crosses the tendon about 9-11 cm proximal to the lateral malleolus. In this configuration, the distance from stimulating cathode 10 to the first electrode (41 or 43) within each electrode pair (41, 42 or 43, 44) is 9.22 cm, and this is the distance used to determine the conduction velocity.

Figure 9:
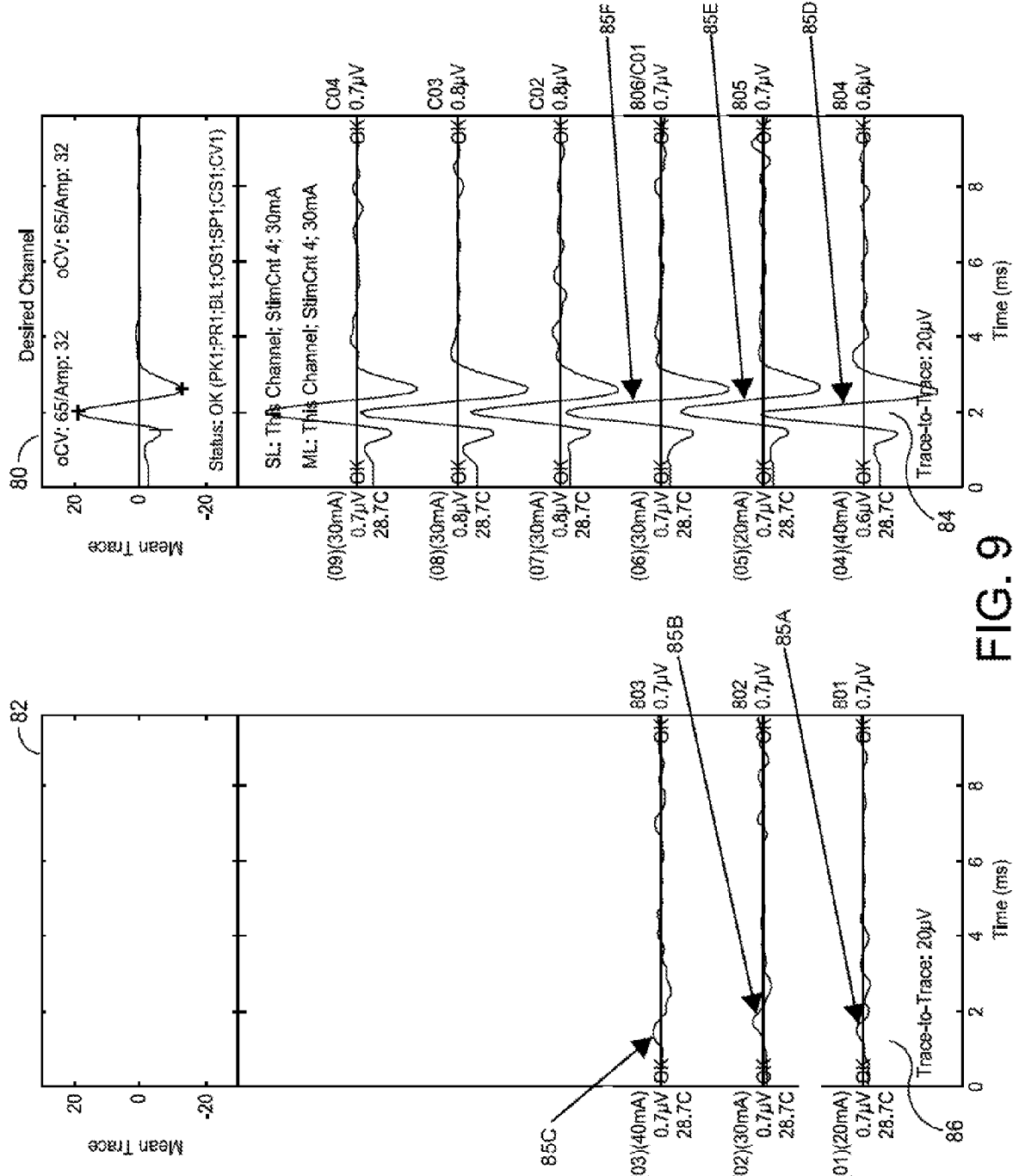
FIG. 9 is a schematic view showing sural nerve responses from two recording channels.

FIG. 9 shows an example of sural nerve responses acquired from the two electrode pairs (41, 42 and 43, 44). The right panel 80 shows the signals 84 recorded from the electrode pair that overlies the nerve, and the left panel 82 shows the signals 86 recorded from the electrode pair that does not overlie the nerve. It will be appreciated that the electrical signals 86 acquired by the "non-intersecting" electrode pair are small compared to the electrical signals acquired by the "intersecting" electrode pair. This is due to the signal-attenuating effects of volume conduction between the sural nerve and the "non-intersecting" electrode pair. By contrast, the signals 84 from the "intersecting" electrode pair are large due to the much smaller distance between the sural nerve and these electrodes.

Thus it will be seen that by providing two parallel electrode pairs 41, 42 and 43, 44, device 1 can automatically adapt to testing either the left leg or the right leg, with the appropriate electrode pair being readily determinable by a comparison of the magnitude of the signals acquired by each electrode pair.

Software

Figure 12:
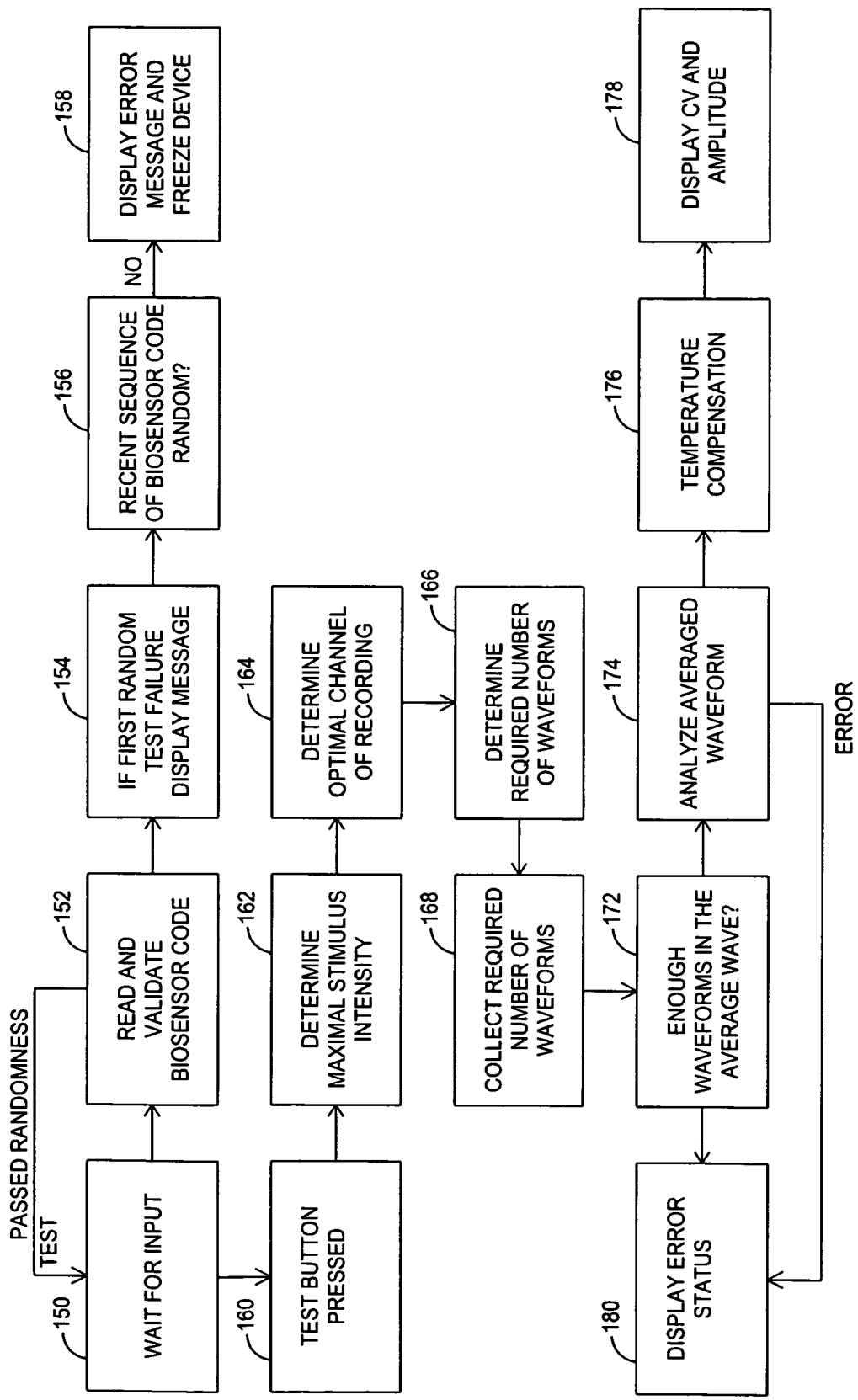
FIG. 12 is a high level functional schematic of the preferred control algorithm for the testing device of FIG. 1.

Device 1 is controlled by a software-based control algorithm which resides on microcontroller 108 (or, alternatively, on an associated storage unit). FIG. 12 provides an overview of various functional blocks of the control algorithm. Upon power up, the control algorithm is in state 150 and waits for an external event, which in the preferred embodiment may be any one of the following: biosensor port insertion, USB port insertion, and test button pressed.

Biosensor Port Insertion

This event is triggered by insertion of a biosensor 30 into biosensor port 16 of device 1. The primary purpose of this software module is to verify that a biosensor is not used across patients. Upon this event trigger, the control algorithm 152 reads the 1-bit biosensor code associated with the inserted biosensor and determines if this code, along with the recent history of earlier biosensor codes, is randomly distributed (which it should be if the biosensor is not being reused, since the biosensors have a randomly distributed 1-bit biosensor code). In the preferred embodiment of the control algorithm, a history of the most recent twenty-four biosensor codes is checked for randomness using the Runs-Test, which is also called the Wald-Wolfowitz test. This test, shown at 154, determines if the series of 0s and 1s in the 24-bit sequence is random to a certain level of specificity. In the preferred embodiment, the target specificity is set at 99%. If any 24-bit sequence is determined to be not random, then a warning message is displayed on device LCD 26, and the 24-bit sequence is reset. If a second 24-bit sequence fails the randomness test (function block 156), then device 1 is locked by function block 158 and no further testing can be performed until device 1 is reset by the manufacturer.

USB Port Insertion

This part of the control algorithm is executed when a USB cable is inserted into USB port 20. Upon detection of this event, the control algorithm goes into the USB communications module which implements a basic serial communication protocol between device 1 and an external device (such as a PC). This USB communications module supports several functions including uploading the most recent test data and downloading a software upgrade.

Test Button Pressed

This part of the control algorithm is executed when test button 22 (FIG. 5) is pressed. Upon detection of this event (function block 160), the control algorithm goes into the test control module which implements a sural nerve conduction test. A sural nerve conduction test is comprised of several sequential steps as described below.

STEP 1. Proper measurement of nerve conduction requires that the nerve is stimulated at the "maximal" level. This "maximal" level is defined as the stimulus intensity such that further increasing of the intensity of the stimulus does not increase the nerve response. In the preferred embodiment (function block 162), this is accomplished by sequentially increasing the stimulus intensity from 20 mA to 60 mA in 10 mA steps. Starting with 30 mA and with each succeeding stimulus intensity, the last two nerve responses are compared with one another. If they are similar in amplitude and shape, as determined by their correlation to one another and to a generic sural nerve response template, then the stimulus intensity is considered to be maximal. In the preferred embodiment, the correlation is implemented as a sum of the products of the two response waveforms (or a response waveform and a generic template), normalized by the square root of the product of the energy in each response waveform (or a response waveform and a generic template). However, if desired, similarity measures different from the correlation technique mentioned above may also be used. If a maximal stimulus intensity is not found, then subsequent data collection is performed at 60 mA.

As described previously, a key object of the present invention is to automatically adapt to measurements from the left or right leg. In order to accomplish this, the sural nerve responses shown in panels 80, 82 (FIG. 9) from the two electrode pairs 41, 42 and 43, 44 are compared during STEP 1 to determine which of the two pairs overlies the nerve and therefore constitutes the optimal recording channel. In the preferred embodiment (function block 164), this is achieved by obtained sural responses from both electrode pairs 41, 42 and 43, 44 under the same stimulus intensity conditions and comparing selected waveform characteristics—specifically, the responses are compared with respect to their amplitude 125, estimated signal-to-noise ratio, and timing of negative peak 124. The electrode pair with a larger amplitude, higher signal-to-noise ratio, and earlier negative peak is selected. In the preferred embodiment, the sural response comparison is performed at two stimulus intensity levels: 40 mA and the maximal stimulus intensity level. If the maximal stimulus intensity level is not found, the comparison occurs at 60 mA. Nerve responses from the selected electrode pair (i.e., 41, 42 or 43, 44) are then used in STEP 2 (below) and STEP 3 (below) for determining the sural nerve response amplitude and conduction velocity.

Additionally, the control algorithm of the preferred embodiment also keeps a history of the selected optimal recording channel from previous tests. More particularly, if a device is preferentially used to test one leg more often than the other leg in a given test environment (e.g., due to user preference, a particular test bed setup, etc.), the corresponding pattern can be easily detected from the history of previous tests. The control algorithm can then utilize this information to improve the test efficiency by starting the data acquisition at the preferred recording channel. As an example, and referring now to FIG. 9, if a test starts at the non-optimal recording channel, waveforms 85A, 85B, 85C will be collected. Since the acquired waveforms will not meet the maximal stimulus intensity criteria, waveform 85D from the other channel will be acquired at 40 mA stimulus intensity. Comparison of waveforms 85C and 85D will lead to subsequent data acquisition from the second recording channel and waveforms 85E and 85F will be collected. Waveforms 85E and 85F will meet maximal stimulation criteria. Therefore, six waveforms (85A, 85B, 85C, 85D, 85E, and 85F) are needed to complete STEP 1 as described above where the test starts on the non-optimal recording channel. Alternatively, and as implemented in the preferred embodiment of the invention, if the control algorithm detects a preferential pattern in the previous test history, it starts the test at the preferential recording channel. Then the waveform acquisition sequence will be different. More particularly, it will start by collecting waveforms 85E and 85F. Since these two waveforms 85E (acquired with 20 mA) and 85F (acquired with 30 mA) will meet the maximal stimulation criteria, the control algorithm will just need to acquire waveform 85B (stimulated with 30 mA) from the alternative recording channel to allow for a comparison between the two recording channels. Therefore, only three waveforms (85E, 85F, and 85B) are required in order to complete STEP 1 when the control algorithm utilizes the optimal recording channel history of previous tests and identifies a preferential recording channel.

STEP 2. Upon determination of the maximal stimulus intensity level, device 1 will repeatedly stimulate the sural nerve at the maximal stimulus intensity level and average the nerve responses into a mean nerve response. In the preferred embodiment (function blocks 166, 168 and 172), the number of waveforms averaged is either 4 or 8 depending on the estimated signal-to-noise ratio of the first nerve response obtained at the maximal stimulus intensity level. If the signal-to-noise ratio is low, then 8 responses are averaged, and if the signal-to-noise ratio is high, then 4 responses are averaged. During waveform averaging, device 1 will exclude responses that are "outliers". In the preferred embodiment of the present invention, outliers are determined by comparing a given response to the running average of prior responses.

Figure 10:
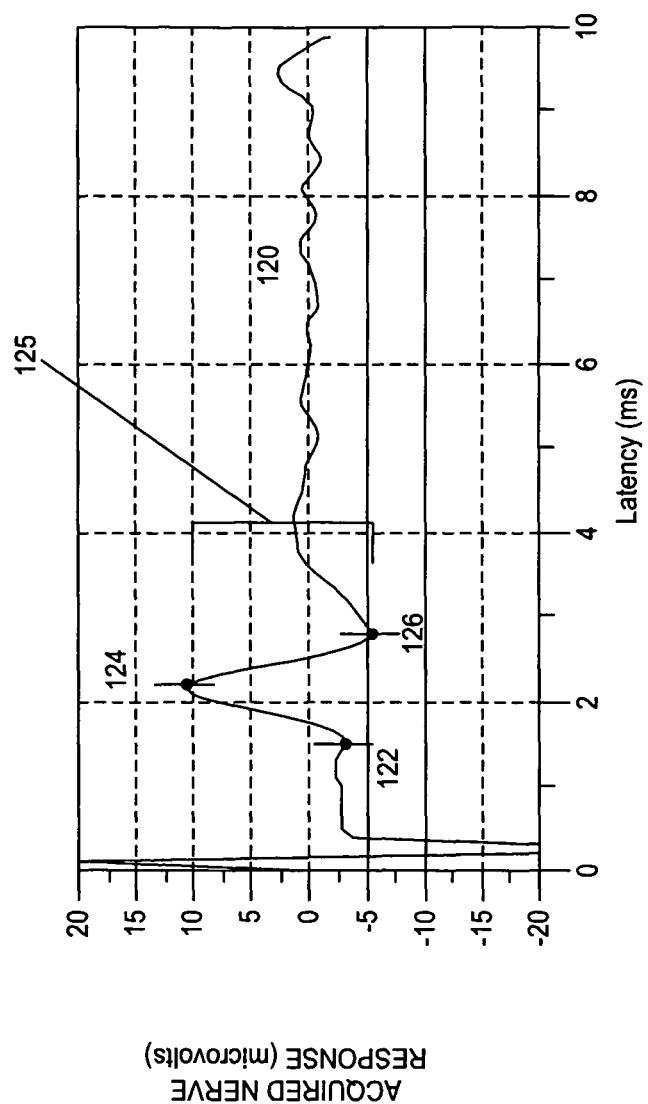
FIG. 10 is an example of an algorithmic analysis of a sural nerve response.
Figure 11:
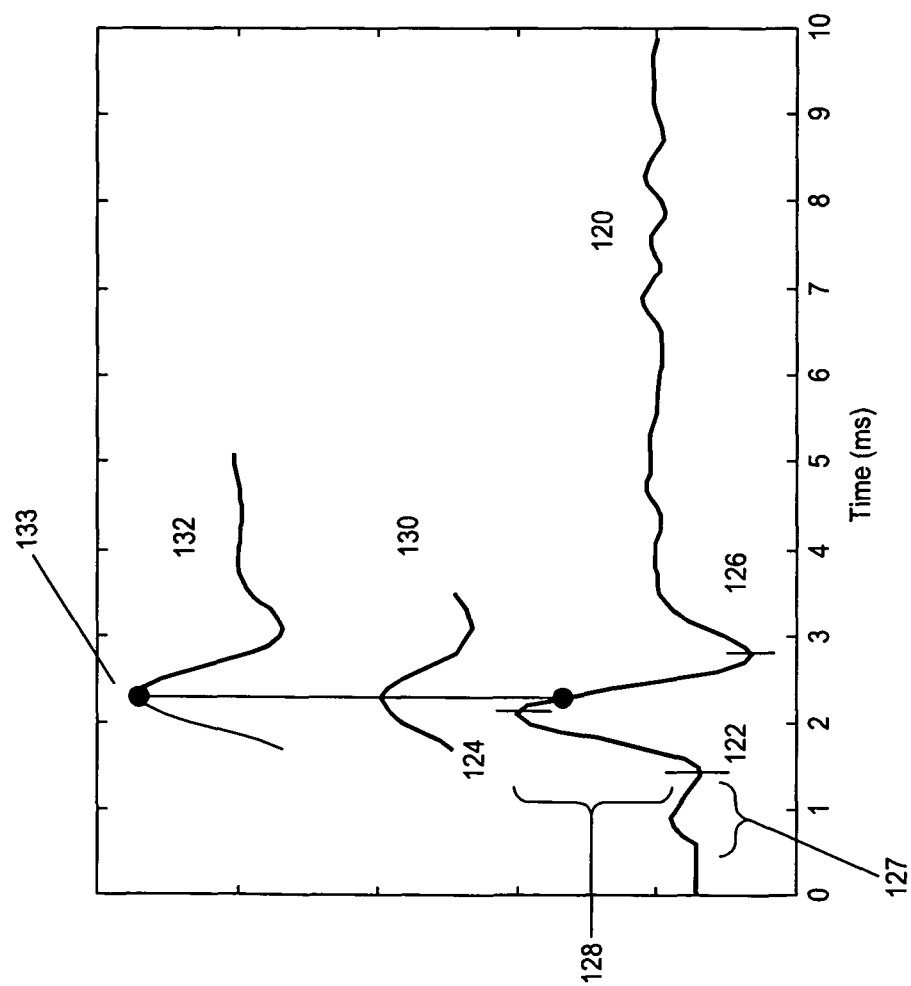
FIG. 11 is an example of how to determine sural nerve response waveform features.

STEP 3. FIG. 10 shows an example of an averaged sural nerve response 120 obtained by device 1. In the preferred embodiment (function block 174), device 1 determines three key waveform features: the nerve response onset 122, the response negative peak 124, and the response positive peak 126. These nerve response features are determined by a signal processing algorithm. The preferred embodiment of this signal processing algorithm is demonstrated through an example waveform shown in FIG. 11. Waveform 120 is a result of averaging one or more sural nerve responses. A generic sural nerve response template 130 is also constructed from a collection of waveforms acquired from multiple test subjects under the same data acquisition conditions (such as filter bandwidth and sampling frequency). As template 130 is slid from left-to-right (denoting a shift in time), a correlation between the shifted template 130 and the averaged waveform 120 at different time shifts can be constructed as the correlation 132. In the preferred embodiment, the correlation is implemented as a sum of the products of the averaged waveform and the shifted template, normalized by the square root of the product of the energy in the averaged waveform 120 and the template 130. However, other forms of correlations may also be used if desired. The algorithm first determines the time 133 at which maximum correlation between the averaged response 120 and a fixed generic sural nerve response template 130 is achieved. The local maximum value of the averaged sural nerve response 120 closest to the correlation peak 133 is identified as the negative peak 124 of the sural response. The positive peak 126 of the sural response is the subsequent local minimum of waveform 120 and is identified by searching a pre-defined window that follows the negative peak 124. Onset 122 is preferably determined by a combination of two methods: curvature and two-line fit. The curvature method identifies the maximum curvature point of the averaged sural nerve response 120 preceding the negative peak 124. The two-line fit method searches for the best common point of two lines that approximate the baseline region 127 and the initial rising edge 128 of average sural nerve waveform 120.

Of course, it should also be appreciated that other techniques well known in the art may be used to determine the nerve response onset 122, the response negative peak 124 and the response positive peak 126.

Once device 1 determines the nerve response onset 122, the response negative peak 124, and the response positive peak 126, the device uses this information to determine (i) conduction velocity (CV), in meters per second, which is calculated as CV=(92.2/Onset), and (ii) the amplitude, in microvolts, which is calculated as the difference in amplitude between the negative peak 124 and positive peak 126. In a preferred embodiment of the present invention (function block 176), the CV is adjusted to compensate for the well known effect of temperature on conduction velocity before the CV is displayed on LCD 26 (FIG. 5). More particularly, during the nerve conduction test, the skin surface temperature of the patient is measured by infrared thermometer 14 (FIG. 3)—preferably one measurement is made with each stimulation. The overall temperature is defined as the median of the 5 individual temperatures. If the median temperature is below 23 degrees C., then an error message is reported to the user and no nerve conduction results are displayed. If the median temperature is 30 degrees C. or greater, then no temperature compensation is performed. For temperatures between 23 and 29.5 degrees C., the CV is corrected according to the following equation:

$$CV_{Displayed} = CV_{Calculated} Q_{10}^{(\Delta T/10)}$$

where $Q_{10}$ is a temperature coefficient and $\Delta T$ is the difference in temperature between 30 degrees C. and the median temperature. The preferred value for $Q_{10}$ is 1.5 based on published scientific studies.

Biosensor Code Incorporated into an Adapter Interposed Between the Tail of the Biosensor and the Biosensor Port of the Testing Device If desired, the 1-bit biosensor code (which may also be referred to as a "reuse code") may be incorporated into an adapter interposed between the tail of the biosensor and the biosensor port of the testing device, rather than being physically incorporated into the biosensor per se. In this form of the invention, the biosensor need not incorporate the traces (e.g., traces 51F and 51G) which are selectively connected/not connected so as to provide the 1-bit biosensor code used to detect reuse of the biosensor. Instead, the traces incorporating the 1-bit biosensor code are carried by the adapter, which also has pass-through traces for electrically connecting the working traces of the biosensor to the testing device. This form of the invention can be advantageous where it is desired to detect biosensor reuse and a biosensor does not already include the means to provide the 1-bit biosensor code.

Modifications

It should also be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A single, fully-integrated, hand-held device for measuring sural nerve conduction velocity and amplitude in either leg of a patient, the device comprising:
a housing adapted to be hand-held by a user, the housing comprising a handle adapted to be gripped by a hand of the user so as to permit the device to be held against either leg of the patient;
a stimulation means resiliently mounted to the housing for electrically stimulating a human sural nerve in either leg of the patient;
a biosensor releasably elastically mounted to the housing, the biosensor comprising a plurality of electrodes physically disposed relative to the housing so as to provide first and second laterally-spaced recording channels for detecting a sural nerve response evoked by the stimulation means in either leg of the patient;
an acquisition means carried by the housing and electrically connected to the biosensor, the acquisition means configured for electrically acquiring the sural nerve response detected by the first and second laterally-spaced recording channels;
a channel determination means for determining which of the first and second laterally-spaced recording channels provides an optimal signal for the sural nerve response;
a processing means carried by the housing and electrically connected to the acquisition means and the channel determination means, the processing means configured for digitizing, processing and storing an acquired sural nerve response provided by the acquisition means and determined by the channel determination means to be the optimal signal for the sural nerve response;
a calculation means carried by the housing and electrically connected to the processing means, the calculation means configured for calculating the sural nerve conduction velocity and amplitude of a processed sural nerve response provided by the processing means; and
a display means carried by the housing for displaying a calculated sural nerve conduction velocity and amplitude provided by the calculation means;
wherein the stimulation means and the biosensor are configured to be held against either leg of the patient, in the vicinity of the sural nerve, by the user manipulating the housing using the handle in the same manner regardless of which leg is being tested.

2. A device according to claim 1 wherein the calculation means is configured to calculate the sural nerve conduction velocity using the onset of the sural nerve response.

3. A device according to claim 1 wherein the calculation means is configured to calculate the sural nerve conduction velocity using the negative peak of the sural nerve response.

4. A device according to claim 1 wherein the device is configured to characterize the sural nerve amplitude by the negative peak-to-positive peak amplitude of the sural nerve response.

5. A device according to claim 1 wherein the device is configured to characterize the sural nerve amplitude by the onset-to-negative peak amplitude of the sural nerve response.

6. A device according to claim 1 wherein the stimulation means comprises two conductive probes, at least one of which is resiliently mounted to the housing.

7. A device according to claim 6 wherein at least one of the said two conductive probes has a variable length which automatically adjusts to the distance between the housing and the patient's leg when the device is held against either of the patient's legs.

8. A device according to claim 1 wherein said biosensor is releasably mounted to said housing by a foam pad that automatically adjusts to the distance between the housing and either of the patient's legs to create a consistent skin contact area when the device is held against either of the patient's legs.

9. A device according to claim 8 wherein the foam pad comprises an adhesive for releasably mounting the biosensor to the foam pad.

10. A device according to claim 8 wherein the foam pad comprises an adhesive for releasably mounting the foam pad to the housing.

11. A device according to claim 1 wherein said device comprises a determination means for determining a maximal stimulus intensity.

12. A device according to claim 11 wherein said determination means is configured to compare sural nerve responses at two stimulus intensities, wherein a second stimulus intensity is greater than a first stimulus intensity.

13. A device according to claim 12 wherein the difference between the two stimulus intensities compared by the determination means is 10 milliamps.

14. A device according to claim 1 wherein the channel determination means determines an optimal sural nerve response recording channel from the first and second laterally-spaced recording channels by determining which channel provides a larger electrical signal and is therefore physically closest to the sural nerve.

15. A device according to claim 1 wherein the processing means is configured to provide identification of the onset, negative peak, and positive peak of the sural nerve response.

16. A device according to claim 1 wherein said device further comprises a non-contact temperature sensor mounted to the housing for measuring a skin surface temperature in the vicinity of the sural nerve.

17. A device according to claim 16 wherein said calculation means is configured to use the skin surface temperature measured by the non-contact temperature sensor to compensate for temperature effects on the sural nerve conduction velocity prior to the sural nerve conduction velocity being displayed by the display means.

18. A device according to claim 16 wherein said calculation means is configured to use the skin surface temperature measured by the non-contact temperature sensor to compensate for temperature effects on the sural nerve amplitude prior to the sural nerve amplitude being displayed by the display means.

19. A device according to claim 16 wherein the calculation means is configured to compare said skin surface temperature measured by the non-contact temperature sensor against a predetermined minimum temperature and, if said skin surface temperature is below the predetermined minimum temperature, then an error message is displayed by the display means.

20. A device according to claim 16 wherein the calculation means is configured to compare said skin surface temperature measured by the non-contact temperature sensor against a predetermined maximum temperature and, if said skin surface temperature is above the predetermined maximum temperature, then an error message is displayed by the display means.

21. A device according to claim 16 wherein the calculation means is configured to compute a variation of said skin surface temperature during a test and to compare the computed variation against a predetermined maximum and, if the computed variation exceeds the predetermined maximum, then an error message is displayed by the display means.

22. A device according to claim 1 wherein the biosensor comprises a male member and the housing comprises a female member, such that when the male member is inserted into the female member, the biosensor is electrically connected to the acquisition means.

23. A device according to claim 22 wherein insertion of said male member of said biosensor into said female member of said housing is electrically detected.

24. A device according to claim 1 wherein said biosensor is coded with a bit pattern.

25. A device according to claim 24 wherein said biosensor is coded with said bit pattern by selectively connecting or not connecting at least two conductive members carried by the biosensor.

26. A device according to claim 24 wherein said bit pattern is a single bit.

27. A device according to claim 24 wherein said a bit pattern is a random bit pattern.

28. A device according to claim 1 wherein the display means includes means for displaying an error message if said sural nerve conduction velocity or amplitude cannot be determined by the calculation means.

29. Apparatus for measuring sural nerve conduction velocity and amplitude, the apparatus comprising:
a housing;
a stimulation means mounted to the housing for electrically stimulating a human sural nerve;
a biosensor releasably mounted to the housing, the biosensor comprising a plurality of electrodes for detecting a sural nerve response evoked by the stimulation means;
an acquisition means mounted to the housing and electrically connected to the biosensor, the acquisition means configured for electrically acquiring the sural nerve response detected by the biosensor;
a processing means mounted to the housing and electrically connected to the acquisition means, the processing means configured for digitizing, processing and storing an acquired sural nerve response provided by the acquisition means;
a calculation means mounted to the housing and electrically connected to the processing means, the calculation means configured for calculating the sural nerve conduction velocity and amplitude of a processed sural nerve response provided by the processing means; and
a display means mounted to the housing for displaying a calculated sural nerve conduction velocity and amplitude provided by the calculation means;
wherein the stimulation means and the biosensor are designed to be placed on a patient's anatomy, in the vicinity of the a sural nerve, by manipulating the housing; and
wherein a recent history of biosensor bit patterns is detected and stored by the apparatus.

30. Apparatus according to claim 29 wherein said recent history is the 24 most recent bit patterns detected by the apparatus.

31. Apparatus according to claim 29 wherein the apparatus is configured to apply a test of randomness to said recent history of biosensor bit patterns.

32. Apparatus according to claim 31 wherein the apparatus is configured to cause a warning to be displayed by the display means if said test of randomness indicates that the recent history of bit patterns is unlikely to be random.

33. Apparatus according to claim 32 wherein the apparatus is configured to be rendered unusable—if said warning has been displayed by the display means and a second test of randomness on a subsequent recent history of bit patterns indicates a lack of randomness.

34. Apparatus according to claim 33 wherein the apparatus is configured to require a reset by the manufacturer prior to further use.

35. Apparatus according to claim 31 wherein said test of randomness applied by the apparatus is the Runs-Test.

36. A single, fully-integrated, hand-held nerve conduction testing device for measuring sural nerve conduction velocity and amplitude in either leg of a patient, the device comprising a hand-held component and a single-patient use biosensor component, wherein the biosensor component is both physically and electrically connected to the hand-held component to acquire a sural nerve response;
wherein the hand-held component comprises a housing adapted to be hand-held by a user the housing comprising a handle adapted to be gripped by a hand of the user so as to permit the device to be held against either leg of the patient, and a stimulation means resiliently mounted to the housing for electrically stimulating a human sural nerve in either leg of the patient;

wherein the single-patient use biosensor component comprises a biosensor unit releasable elastically mounted to the housing, the biosensor unit comprising a plurality of electrodes physically disposed relative to the housing so as to provide first and second laterally-spaced recording channels when the biosensor unit is mounted to the housing for acquiring the sural nerve response evoked by the stimulation means in either leg of the patient;

wherein the hand-held component further comprises an acquisition means carried by the housing and electrically connected to the biosensor unit, the acquisition means configured for electrically acquiring the sural nerve response detected by the first and second laterally-spaced recording channels, a channel determination means for determining which of the first and second laterally-spaced recording channels provides an optimal signal for the sural nerve response, a processing means carried by the housing and electrically connected to the acquisition means and the channel determination means, the processing means configured for digitizing, processing and storing an acquired nerve response provided by the acquisition means and determined by the channel determination means to be the optimal signal for the sural nerve response, a calculation means carried by the housing and electrically connected to the processing means, the calculation means configured for calculating the sural nerve conduction velocity and amplitude of a processed nerve response provided by the processing means, and a display means carried by the housing for displaying a calculated sural nerve conduction velocity and amplitude provided by the calculating means; and wherein the stimulation means and the biosensor unit are configured to be held against either leg of the patient, in the vicinity of the sural nerve, by the user manipulating the housing using the handle in the same manner regardless of which leg is being tested.

37. A device according to claim 36 wherein the stimulation means comprises:

a pair of stimulating electrodes, at least one of the stimulating electrodes having an adjustable height, to deliver electrical current to the patient so as to stimulate the sural nerve under a varying surface anatomy.

38. A device according to claim 36 wherein the hand-held component comprises a biosensor port to provide electrical connection to the biosensor component which is physically attached to the hand-held component through an adhesive-coated foam pad.

39. A device according to claim 36 wherein the stimulation means comprises a pair of stimulation probes, wherein at least one of the probes is spring-mounted so as to allow full and complete contact between a tip of the probe and a skin surface of uneven height of either leg of the patient.

40. A device according to claim 36 further comprising a temperature sensing probe mounted to the housing so as to allow skin temperature measurements.

41. A device according to claim 36 further comprising a pad made of a flexible material positioned between the housing and the biosensor unit.

42. A device according to claim 41 further comprising an adhesive coating on each side of the pad to provide a secure but not permanent bond between (i) the pad and the housing, and (ii) the pad and the biosensor unit.

43. A device according to claim 36 wherein an electrical connection between the hand-held component and the biosensor component is achieved by connecting a female connector disposed on the hand-held component and a male connector disposed on the biosensor component.

44. A device according to claim 36 wherein the biosensor unit comprises at least two pairs of active electrodes.

45. A device according to claim 44 wherein the at least two pairs of active electrodes are configured so that at least one pair of active electrodes will overlay the sural nerve for detection of the sural a nerve response evoked by the stimulation means.

46. A device according to claim 36 wherein the biosensor unit comprises a plurality of traces, at least two of which are not connected to electrodes.

47. Apparatus according to claim 46 wherein the traces not connected to electrodes form various combinational patterns among them and are decoded by electronics embedded in the housing.

48. A device according to claim 47 wherein the various combinational patterns are configured to provide a means for automatically recognizing at least one of:

proper connection of the biosensor component to the hand-held component; the identification of the biosensor model being connected to the housing; or identification of the biosensor manufacturer.

49. A device according to claim 36 further comprising a software control module configured to automatically detect the electrical connection of the biosensor unit with the housing and initiate proper test setups based on biosensor type.

50. A device according to claim 49 wherein said software control module is configured to recognize a predetermined characteristic of the biosensor unit.

51. A device according to claim 50 wherein said software control module is configured to use the predetermined characteristic of the biosensor unit to determine a likelihood that the biosensor unit has been re-used across multiple patients through an analysis of a retained biosensor unit characteristic history from each biosensor unit electrical connection.

52. A device according to claim 36 further comprising a software control module configured to automatically determine a stimulus intensity level that the stimulation means must generate to evoke a maximum sural nerve response by analyzing the sural nerve responses acquired by the acquisition means and by controlling subsequent stimulus intensity levels.

53. A device according to claim 52 wherein the software control module is configured to analyze waveform features of the acquired sural nerve response, where the waveform features include amplitude, negative peak time, similarity of the sural nerve response waveform to a known template, and similarity of the sural nerve response waveform to the sural nerve response waveform acquired at lower stimulus intensity.

54. A device according to claim 36 wherein said channel determination means is configured to select a preferred recording channel from the first and second laterally-spaced recording channels by analyzing a collection of sural nerve response waveform features from the sural nerve response detected by the first and second laterally-spaced recording channels and acquired by the acquisition means.

55. A device according to claim 54 wherein the collection of sural nerve response waveform features analyzed by the channel determination means includes amplitude, signal-to-noise ratio, negative peak time, and nerve response waveform conformity to a known template.

56. A device according to claim 54 further comprising a software control module that analyzes the frequency distribution of the collection of sural nerve response waveform features detected by the recording channel that has been selected as the preferred recording channel in prior tests so as to determine which electrode recording pair associated with the preferred recording channel is more likely to overlay the sural nerve.

57. A device according to claim 56 wherein said software control module is configured to change a default electrode pair.

58. A device according to claim 36 further comprising a software control module configured to predict a number of sural nerve responses needed to form an averaged nerve response by estimating a noise level based on a sural nerve response waveform segment prior to the onset of stimulation and by estimating the amplitude of the sural nerve response evoked by maximal stimulation.

59. A device according to claim 36 further comprising a software control module configured to reject outlier sural nerve response waveforms when multiple sural nerve response waveforms are being acquired for the purpose of forming an averaged sural nerve response waveform.

60. A device according to claim 59 wherein the device is configured to classify an individual sural nerve response waveform as one of the outlier sural nerve response waveforms if its correlation to a running average of sural nerve response waveforms is below a threshold or if the individual sural nerve response waveform possesses a large percentage of extreme values based on a time-locked comparison of multiple sural nerve response waveforms.

61. A device according to claim 59 wherein the software control module is further configured to analyze the averaged sural nerve response waveform to identify predetermined sural nerve response features.

62. A device according to claim 61 wherein the predetermined sural nerve response features analyzed by the software control module comprise at least one selected from the group consisting of signal onset, negative peak and positive peak.

63. A device according to claim 62 wherein the predetermined sural nerve response features are used to determine the sural nerve conduction parameters of onset conduction velocity and peak-to-peak amplitude.

64. A device according to claim 36 further comprising a non-contact temperature sensor wherein the non-contact temperature sensor continuously obtains temperature measurements of the skin near the sural nerve when it is being stimulated.

65. A device according to claim 64 further comprising a software control module, wherein the software control module is configured to analyze the obtained temperature measurements to determine the reliability of the temperature measurements and the appropriateness of a test condition.

66. A device according to claim 65 wherein said software control module is configured to calculate statistics including standard deviation and median value of the temperature measurements.

67. A device according to claim 66 wherein, when the standard deviation exceeds a predetermined threshold, said software control module is configured to discard test results.

68. A device according to claim 66 wherein, when the median temperature is below a predetermined threshold, said software control module is configured to also discard the test results.

69. A device according to claim 64 further comprising a software control module configured to automatically compensate for measured sural nerve conduction velocity as a result of low skin temperature.

70. A device according to claim 69 wherein the software control module is configured to direct the calculation means to compensate for changes in sural nerve conduction velocity due to skin temperature using a table of predetermined values.

71. A single, fully-integrated, hand-held nerve conduction testing device for measuring sural nerve conduction velocity and amplitude in either leg of a patient, the device comprising a hand-held component and a single-patient use biosensor component, wherein the biosensor component is both physically and electrically connected to the hand-held component to acquire a sural nerve response;
  wherein the hand-held component comprises a housing adapted to be hand-held by a user, the housing comprising a handle adapted to be gripped by a hand of the user so as to permit the device to be held against either leg of the patient, and a stimulation means resiliently mounted to the housing for electrically stimulating a human sural nerve in either leg of the patient;
  wherein the single-patient use biosensor component comprises a biosensor unit releasably elastically mounted to the housing, the biosensor unit comprising a plurality of electrodes for detecting a sural nerve response evoked by the stimulation means in either leg of the patient;
  wherein the hand-held component further comprises an acquisition means carried by the housing and electrically connected to the biosensor unit, the acquisition means configured for electrically acquiring the sural nerve response detected by the biosensor unit, a processing means carried by the housing and electrically connected to the acquisition means, the processing means configured for digitizing, processing and storing an acquired nerve response provided by the acquisition means, a calculation means carried by the housing and electrically connected to the processing means, the calculation means configured for calculating the sural nerve conduction velocity and amplitude of a processed nerve response provided by the processing means, and a display means carried by the housing for displaying a calculated sural nerve conduction velocity and amplitude provided by the calculating means; and
  wherein the stimulation means and the biosensor unit are configured to be held against either leg of the patient, in the vicinity of the sural nerve, by the user manipulating the housing using the handle;
  wherein the device further comprises a software control module that automatically detects the connection of the biosensor unit with the housing and initiates proper test setups based on biosensor type;
  wherein said software control module recognizes a predetermined characteristic of the biosensor unit; and
  wherein said software control module uses the predetermined characteristic of the biosensor unit to determine the likelihood that the biosensor unit has been re-used across multiple patients through the analysis of a retained biosensor unit characteristic history from each biosensor unit connection.

* * * * *